US012728199B2

(12) United States Patent
Pirbodaghi et al.

(10) Patent No.: US 12,728,199 B2
(45) Date of Patent: Sep. 8, 2026

(54) NEEDLE INSERTION MECHANISM FOR DRUG DELIVERY DEVICE

(71) Applicant: AMGEN INC., Thousand Oaks, CA (US)

(72) Inventors: Tohid Pirbodaghi, Cambridge, MA (US); Samin Akbari, Cambridge, MA (US); Joshua Tamsky, Los Angeles, CA (US); Paul Daniel Faucher, Escondido, CA (US); Scott Robert Gibson, Simi Valley, CA (US); Sheldon B. Moberg, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 850 days.

(21) Appl. No.: 17/641,458

(22) PCT Filed: Oct. 5, 2020

(86) PCT No.: PCT/US2020/054201

§ 371 (c)(1),
(2) Date: Mar. 22, 2022

(87) PCT Pub. No.: WO2021/071763

PCT Pub. Date: Apr. 15, 2021

(65) Prior Publication Data

US 2022/0355025 A1 Nov. 10, 2022

Related U.S. Application Data

(60) Provisional application No. 62/911,700, filed on Oct. 7, 2019.

(51) Int. Cl.
*A61M 5/142* (2006.01)
*A61M 5/172* (2006.01)

(52) U.S. Cl.
CPC ........ *A61M 5/14248* (2013.01); *A61M 5/172* (2013.01); *A61M 2005/14252* (2013.01); *A61M 2205/0266* (2013.01)

(58) Field of Classification Search
CPC .... A61M 5/14248; A61M 2005/14252; A61M 2005/1585; A61M 5/3287; A61M 5/3291;
(Continued)

(56) References Cited

U.S. PATENT DOCUMENTS 9,511,189 B2 12/2016 O'Connor et al.
2006/0142698 A1 6/2006 Ethelfeld
(Continued)

FOREIGN PATENT DOCUMENTS

EP 3260151 A1 * 12/2017
WO WO-2013149186 A1 * 10/2013 ......... A61B 5/14532
(Continued)

OTHER PUBLICATIONS

International Search Report of International Application No. PCT/US2020/054201, dated Feb. 9, 2021.
(Continued)

*Primary Examiner* — Lauren P Farrar
(74) *Attorney, Agent, or Firm* — MARSHALL, GERSTEIN & BORUN LLP

(57) ABSTRACT

A drug delivery device includes a housing, a container disposed in the housing, an activation mechanism, and a needle insertion mechanism (NIM). The container has an inner volume to contain a medicament which is urged out of the container by the activation mechanism. The needle insertion mechanism (NIM) is operably coupled with the activation mechanism and includes an actuation assembly adapted to insert a needle and a cannula to deliver the medicament from the container. The actuation assembly is movable between a storage state, a first operational state, a
(Continued)

second operational state, and a third operational state to selectively position the needle and the cannula.

20 Claims, 17 Drawing Sheets

(58) Field of Classification Search
CPC .. A61M 2205/0266; A61M 2039/0279; A61M 2039/0282; A61M 2039/0276; A61M 5/2033; A61M 2005/206; A61M 5/20
See application file for complete search history.

(56) References Cited

U.S. PATENT DOCUMENTS

| | | | | |
|---|---|---|---|---|
| 2017/0224915 | A1 | 8/2017 | Destefano et al. | |
| 2019/0275241 | A1 | 9/2019 | Ring et al. | |
| 2019/0351143 | A1 | 11/2019 | Egloff et al. | |
| 2019/0365993 | A1* | 12/2019 | Staub | A61M 5/3287 |
| 2020/0384197 | A1* | 12/2020 | Chiu | A61M 5/16831 |

FOREIGN PATENT DOCUMENTS

| | | | | |
|---|---|---|---|---|
| WO | WO-2018096149 | A1 | 5/2018 | |
| WO | WO-2018165499 | A1 * | 9/2018 | A61M 5/14248 |

OTHER PUBLICATIONS

Written Opinion of the International Searching Authority for International Application No. PCT/US2020/054201, dated Feb. 9, 2021.
European Patent Application No. 20799876.6, Communication pursuant to Article 94(3) EPC, dated Feb. 12, 2025.

* cited by examiner

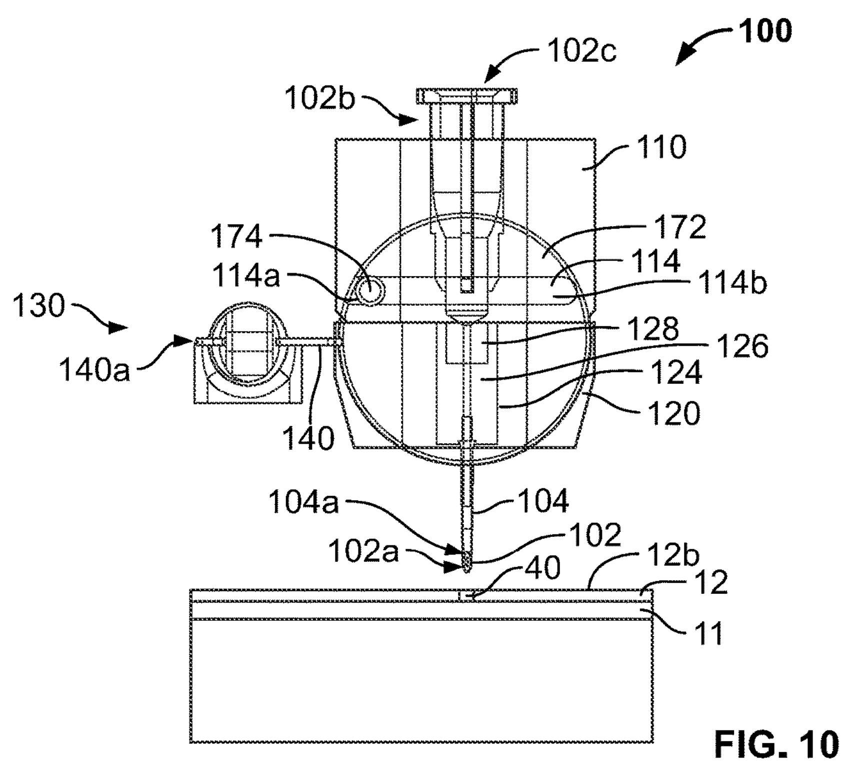
FIG. 10
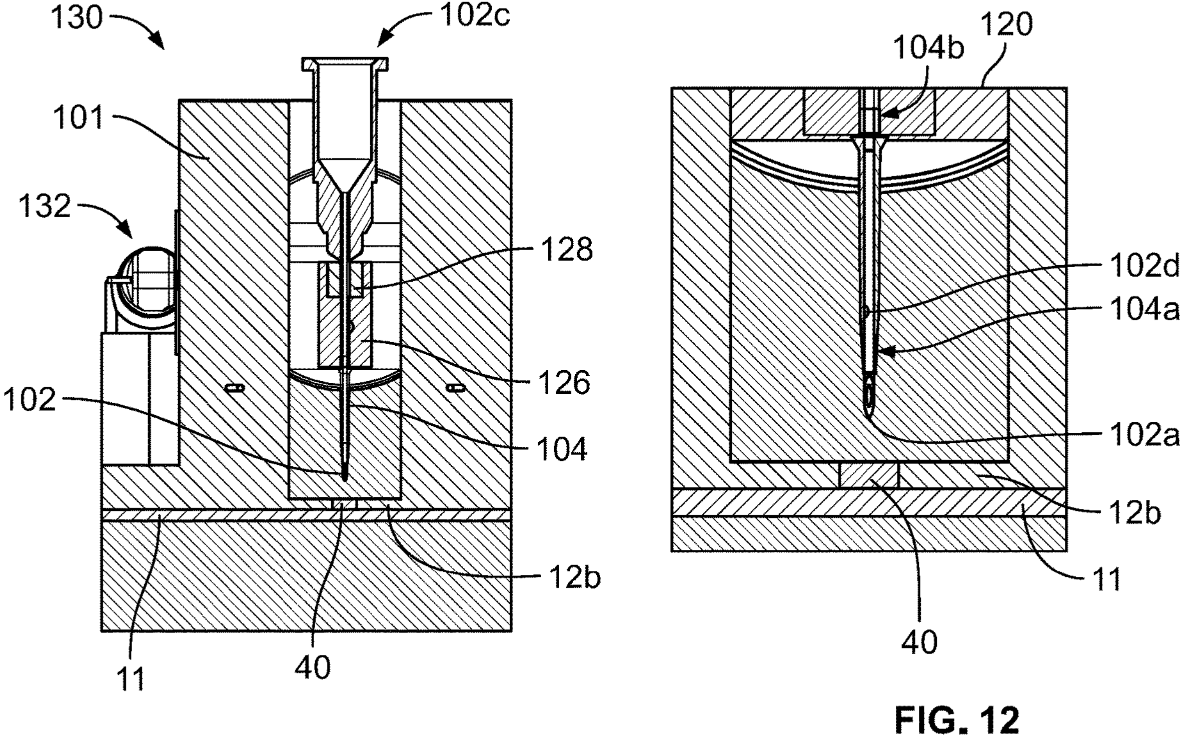
FIG. 11
FIG. 12

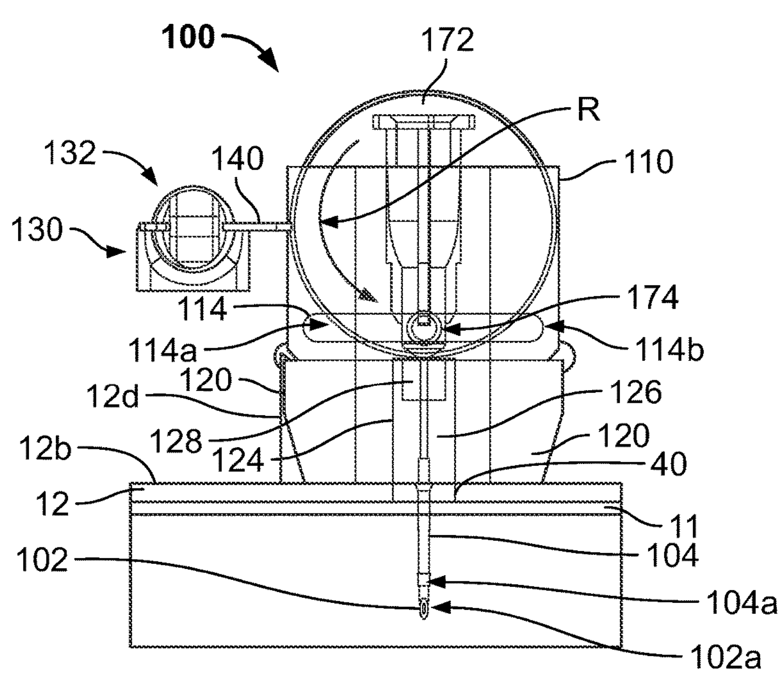
FIG. 15
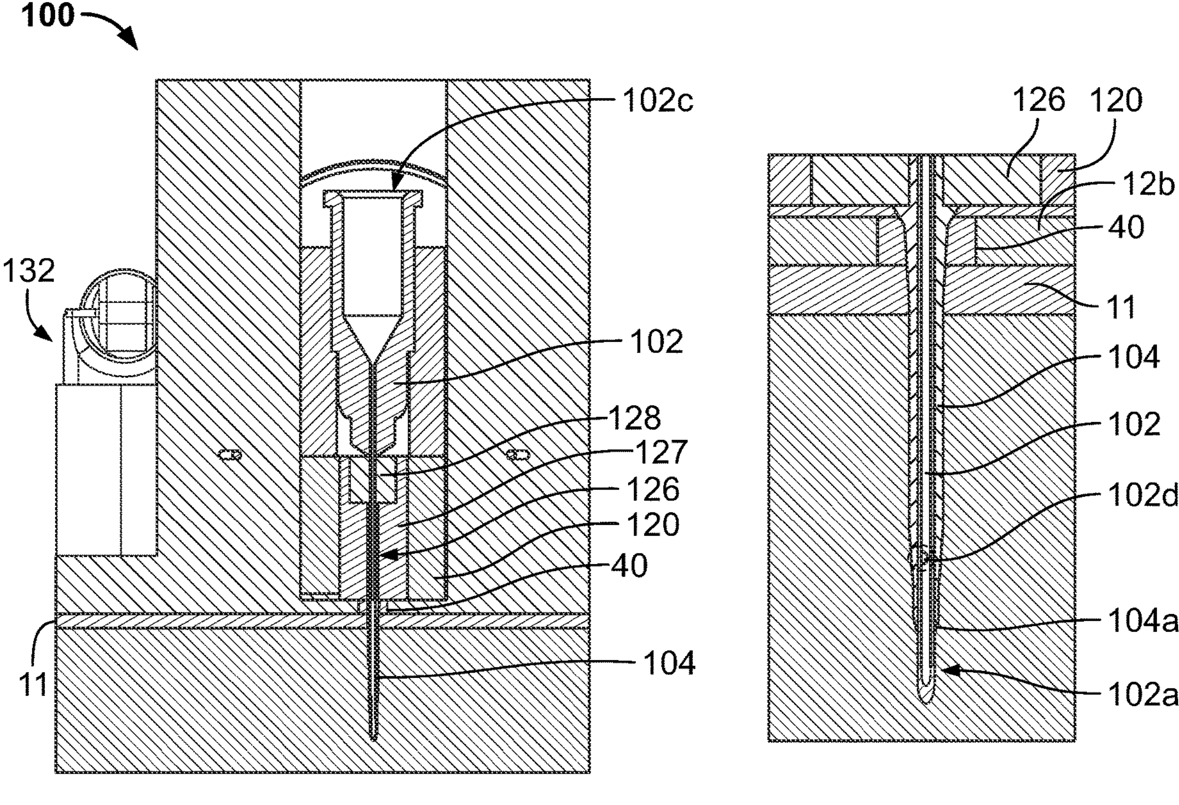
FIG. 16
FIG. 17

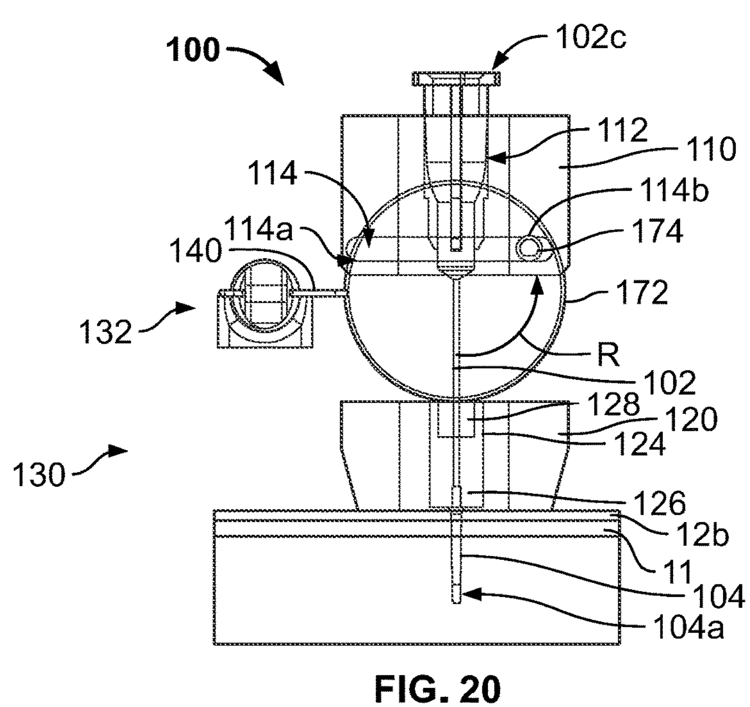
FIG. 20
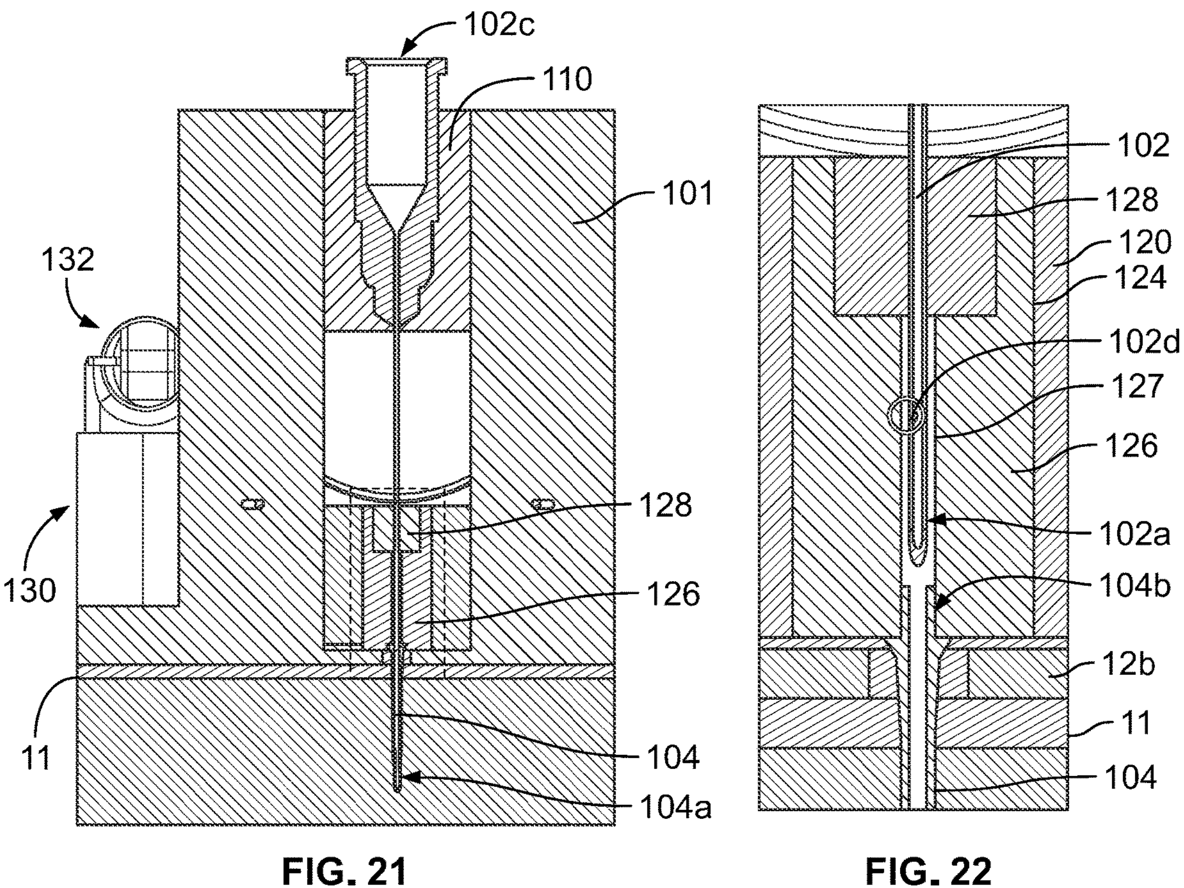
FIG. 21
FIG. 22

102c
172
110
165
168
178
164
R
170
162
144
162a
120
132
166
140
12d
130
12b
11
134

102c
100
112
114
110
114a
114b
174
140
132
172
R
102
128
130
120
126
12b
11
104
104a

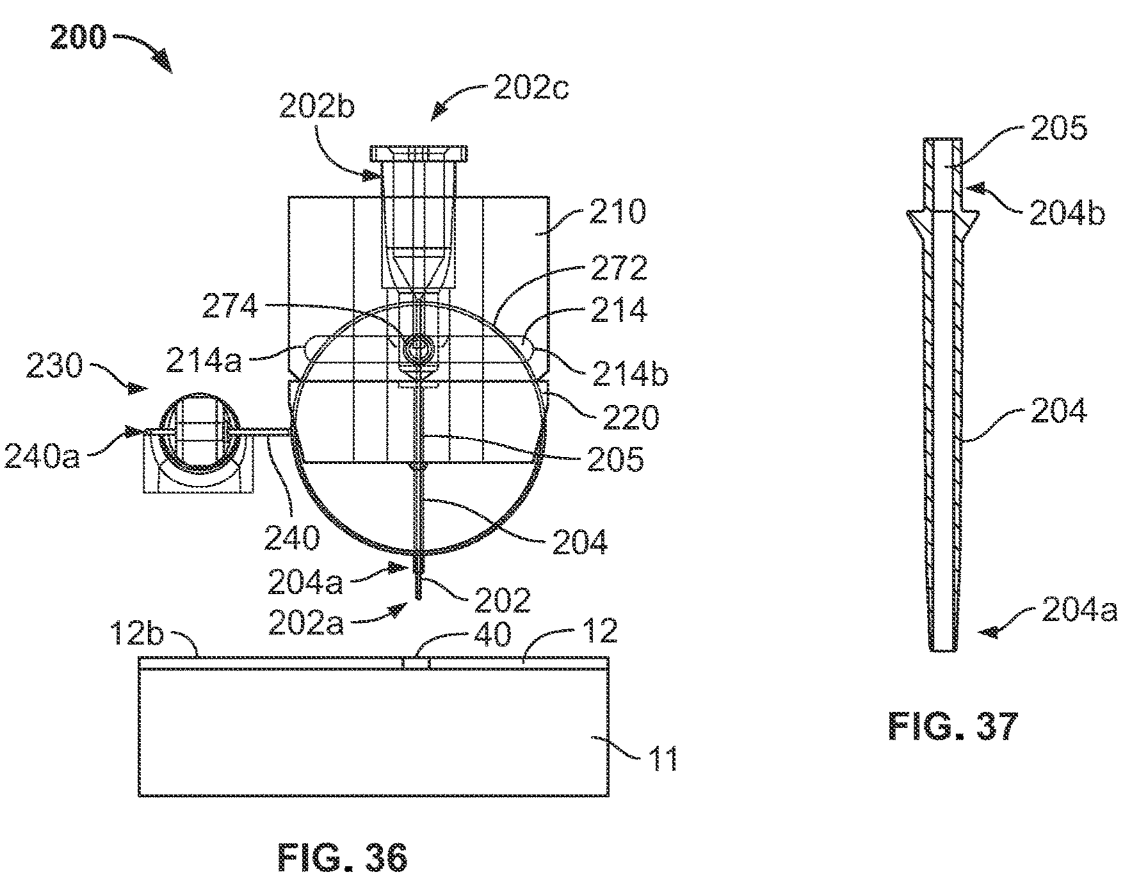
FIG. 36
FIG. 37
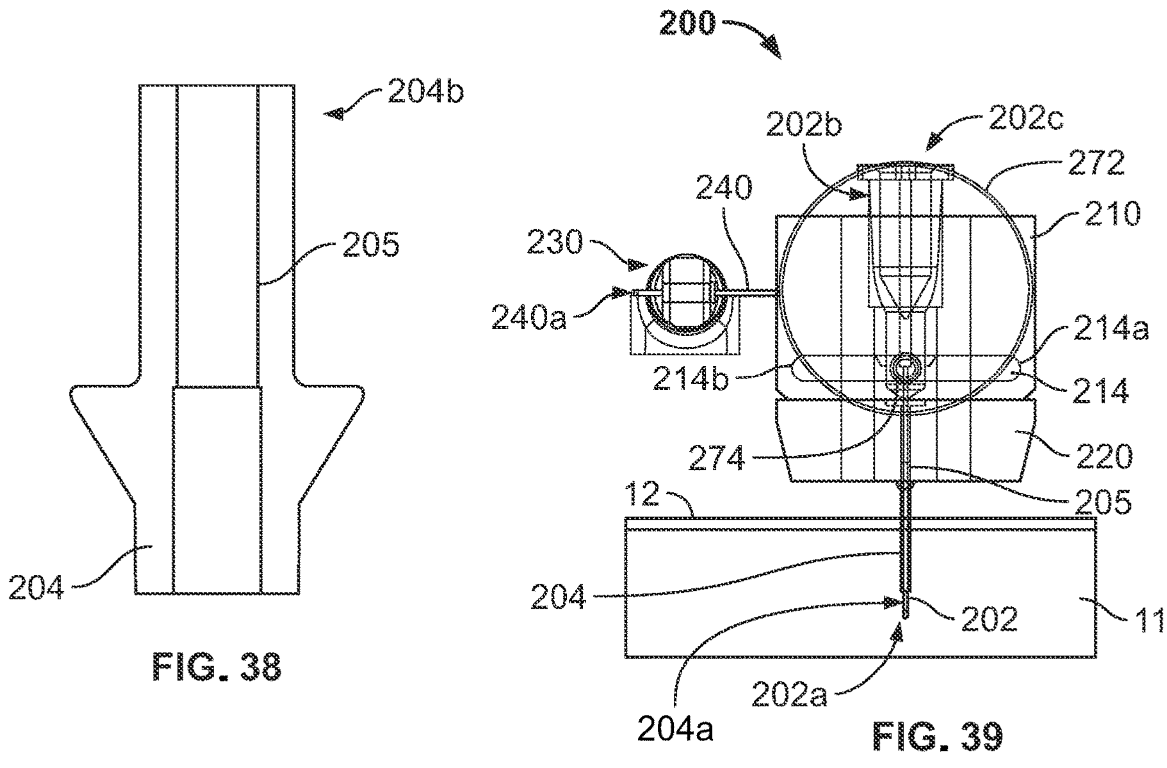
FIG. 38
FIG. 39

NEEDLE INSERTION MECHANISM FOR DRUG DELIVERY DEVICE

CROSS REFERENCE TO RELATED APPLICATION

This is the United States national phase of International Patent Application No. PCT/US20/54201, filed Oct. 5, 2020, which claims priority to U.S. Provisional Patent Application No. 62/911,700, filed Oct. 7, 2019, the entire contents of each of which hereby being incorporated by reference herein.

FIELD OF DISCLOSURE

The present disclosure generally relates to drug delivery devices and, more particularly, to drug delivery devices having multi-stage actuation assemblies to assist in drug flow.

BACKGROUND

Drug delivery devices, such as injectors, are used to deliver liquid drugs to a patient. Upon activation, a drug delivery device may expel a drug stored within an internal reservoir of a primary container through a needle, cannula, or other delivery member into the patient. Some drug delivery devices may be temporarily attached to a patient to deliver a drug via an injection needle or some other means over an extended period of time. The drug delivery device may be adhesively attached to the tissue of the patient's abdomen, thigh, arm, or some other portion of the patient's body.

Clots in the fluid path may occur, and occlusions may form within the fluid path of the drug delivery device. The coagulated material may prevent the drug from being delivered when the pressure required to push the medication through the clot (or to alternatively displace the clot) exceeds the drive force capability of the device. Accordingly, the drug delivery device may stall, which can adversely impact delivery of the drug to the user, particularly with respect to delayed delivery devices. Delayed delivery devices may enhance therapeutic efficacy of certain drugs while preventing adverse side effects. Such devices may first be activated by a healthcare professional, thereby causing a needle and/or a cannula to be inserted into a patient's tissue, but may not administer the drug until after a predetermined delay.

As described in more detail below, the present disclosure sets forth systems for delivery devices embodying advantageous alternatives to existing systems and methods, and that may address one or more of the challenges or needs mentioned herein, as well as provide other benefits and advantages.

SUMMARY

In accordance with a first aspect, a drug delivery device includes a housing, a container disposed in the housing, an activation mechanism, and a needle insertion mechanism (NIM). The container has an inner volume to contain a medicament which is urged out of the container by the activation mechanism. The needle insertion mechanism (NIM) is operably coupled with the activation mechanism and includes an actuation assembly adapted to insert a needle and a cannula to deliver the medicament from the container. The actuation assembly is movable between a storage state, a first operational state, a second operational state, and a third operational state to selectively position the needle and the cannula.

In some approaches, in the first operational state, the actuation assembly moves at least one of the needle or the cannula to an extended position. In the second operational state, the actuation assembly moves at least one of the needle or the cannula to a medicament flow restricting position. In the third operational state, the actuation assembly moves at least one of the needle or the cannula to a medicament flow permitting position.

In some of these examples, the actuation assembly can include an escapement assembly and a rotatable link mechanism. The escapement assembly includes a driving member, an urging member operably coupled with the driving member, and a pivotable member operably coupled with the urging member. The rotatable link mechanism is selectively coupled with the pivotable member and is rotatable between a storage position, a first position, a second position, and a third position. The driving member may be in the form of an electromechanical actuator (such as, for example, a shape-memory muscle wire) that contracts upon receiving an electrical signal to compress the urging member, thereby selectively pivoting the pivotable member.

In some forms, the rotatable link mechanism may include a first timing disk and a second timing disk. The first timing disk has a first engagement tab and a second engagement tab. The second timing disk has a third engagement tab and a fourth engagement tab. The pivotable member selectively engages the first engagement tab, the second engagement tab, the third engagement tab, and the fourth engagement tab to position the actuation assembly between the storage state, the first operational state, the second operational state, and the third operational state. In some examples, the rotatable link mechanism further includes a drive pin. The drive pin is movable between a storage position when the actuation assembly is in the storage state, a first position when the actuation assembly is in the first operational state, a second position when the actuation assembly is in the second operational state, and a third position when the actuation assembly is in the third operational state. Movement of the drive pin selectively moves the needle and the cannula. In some examples, a second resilient member is operably coupled with the rotatable link mechanism to urge the rotatable link mechanism from the storage state to the first, second, and third positions.

In some forms, the needle insertion mechanism (NIM) may include a needle yoke and a cannula yoke, each of which is operably coupled with the actuation assembly. The needle yoke includes a needle coupling portion to receive a portion of the needle, and the cannula yoke includes a cannula coupling portion to receive a portion of the cannula.

In accordance with a second aspect, an activation mechanism for a drug delivery device includes an escapement assembly and a rotatable link mechanism. The escapement assembly includes a driving member, an urging member operably coupled with the driving member, and a pivotable member operably coupled with the urging member. The rotatable link mechanism is selectively coupled with the pivotable member. The activation mechanism is movable between a storage state whereby the rotatable link mechanism is in a storage position, a first operational state whereby the rotatable link mechanism is in a first position, a second operational state whereby the rotatable link mechanism is in a second position, and a third operational state whereby the rotatable link mechanism is in a third position.

BRIEF DESCRIPTION OF THE DRAWINGS

The above needs are at least partially met through provision of the needle insertion mechanism (NIM) for a drug delivery device described in the following detailed description, particularly when studied in conjunction with the drawings, wherein:

The accompanying figures show embodiments according to the disclosure and are exemplary rather than limiting.

FIG. 10 illustrates a side elevation view of a portion of the example needle insertion mechanism (NIM) of FIGS. 8 and 9 in the storage state in accordance with various embodiments;

FIG. 11 illustrates a side elevation sectioned view of a portion of the example needle insertion mechanism (NIM) of FIGS. 8-10 in the storage state in accordance with various embodiments;

FIG. 12 illustrates a close-up side elevation sectioned view of the example needle insertion mechanism (NIM) of FIGS. 8-11 in the storage state in accordance with various embodiments;

FIG. 15 illustrates a side elevation view of a portion of the example needle insertion mechanism (NIM) of FIGS. 13 and 14 in the transitory state in accordance with various embodiments;

FIG. 16 illustrates a side elevation sectioned view of a portion of the example needle insertion mechanism (NIM) of FIGS. 13-15 in the transitory state in accordance with various embodiments;

FIG. 17 illustrates a close-up side elevation sectioned view of the example needle insertion mechanism (NIM) of FIGS. 13-16 in the transitory state in accordance with various embodiments;

FIG. 20 illustrates a side elevation view of a portion of the example needle insertion mechanism (NIM) of FIGS. 18 and 19 in the first operational state in accordance with various embodiments;

FIG. 21 illustrates a side elevation sectioned view of a portion of the example needle insertion mechanism (NIM) of FIGS. 18-20 in the first operational state in accordance with various embodiments;

FIG. 22 illustrates a close-up side elevation sectioned view of the example needle insertion mechanism (NIM) of FIGS. 18-21 in the first operational state in accordance with various embodiments;

FIG. 36 illustrates a side elevation view of a second example needle insertion mechanism (NIM) having an alternative sealing mechanism in a storage state in accordance with various embodiments;

FIG. 37 illustrates a side elevation sectioned view of the alternative sealing mechanism of the second example needle insertion mechanism (NIM) of FIG. 36 in accordance with various embodiments;

FIG. 38 illustrates a close-up side elevation sectioned view of the example sealing mechanism of FIGS. 36 and 37 in accordance with various embodiments;

FIG. 39 illustrates a side elevation view of the second example needle insertion mechanism (NIM) of FIGS. 36-38 in the transitory state in accordance with various embodiments;

Figure 1:
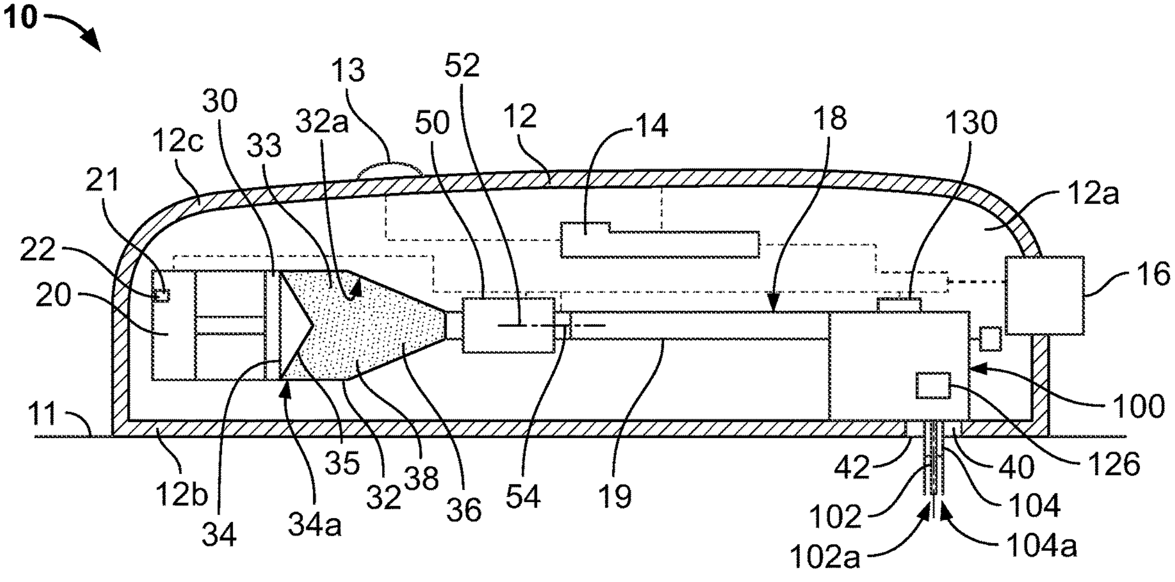
FIG. 1 illustrates a schematic representation of an example arrangement of a drug delivery device in accordance with various embodiments.
Figure 2:
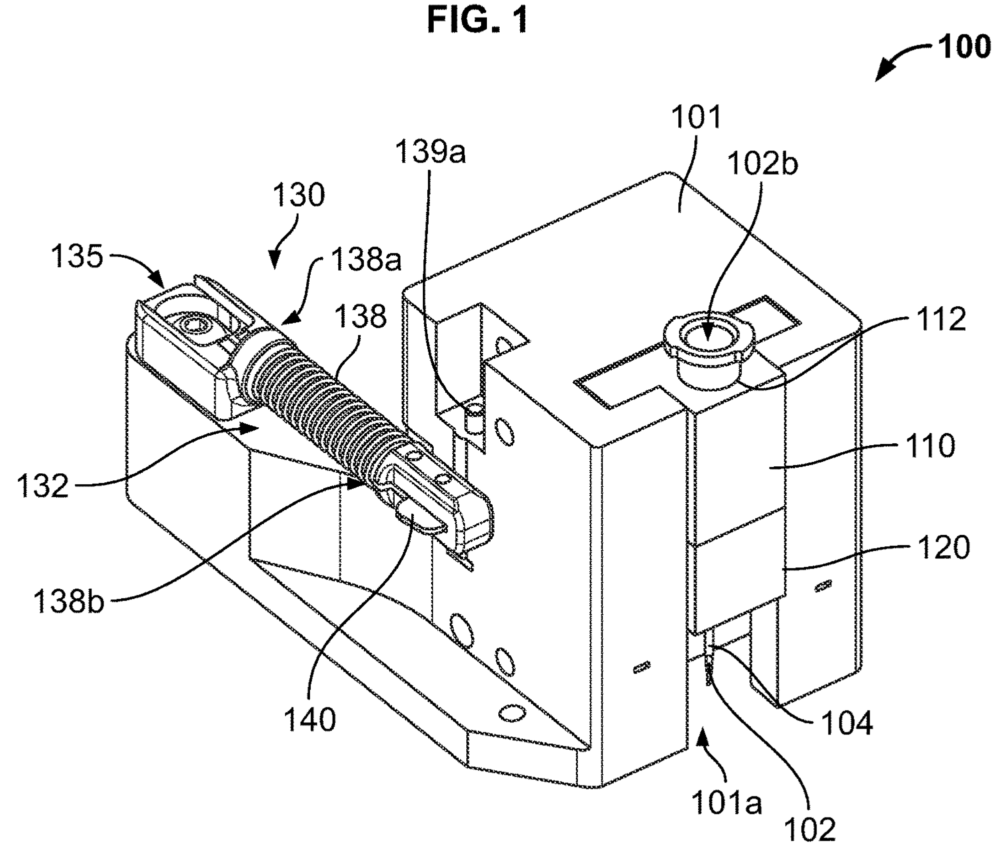
FIG. 2 illustrates an example needle insertion mechanism (NIM) having an actuation assembly for the example drug delivery device of FIG. 1 in the form of a multi-stage Scotch yoke slide valve mechanism in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a drive system for a drug delivery device that includes a multi-stage needle insertion mechanism (NIM) that performs needle insertion and retraction. The system additionally includes a backflow prevention mechanism to prevent ingress of fluids (e.g., bodily fluids) into the drug delivery device. The drug delivery device may include a housing defining a shell and an inner volume, an activation mechanism, a container including a reservoir filled or adapted to be filled with a drug, a needle insertion mechanism (NIM), a fluid flow connection, and a backflow prevention mechanism in the form of a valve, each of which is at least partially disposed within the housing. The valve is in fluid communication with the fluid flow connection and is movable between first and second positions. By incorporating the valve into the needle insertion mechanism (NIM), the needle insertion mechanism (NIM) can selectively insert a needle and/or a cannula into the patient, close the valve to prevent the ingress and/or egress of fluids, and after a pre-determined delay, open the valve to deliver the drug or medicament from the container via the fluid flow connection.

The drug delivery devices described herein may have a delayed delivery, and as such, the needle and cannula may be inserted prior to drug delivery. Accordingly, upon insertion of the needle and/or the cannula, the needle insertion assembly moves the valve to a closed first position whereby fluid flow is restricted. At a later time, the needle insertion assembly urges the valve to a second position whereby fluid may flow through the needle and/or cannula. The valve is a fluid path element disposed in the fluid path that selectively restricts and permits fluid flow through the needle and/or cannula. After the cannula is inserted, yet prior to drug delivery, the valve design allows the fluid flow path to remain sealed against the ingress of fluids (e.g., bodily fluids), thus reducing the likelihood of clogs or clots in the fluid path. Such a design is particularly advantageous for drug delivery devices having non-primed (air filled) fluid paths.

Referring to the Figures, a general drug delivery device 10 is provided that may include any number of aspects of the backflow prevention arrangement herein described. In some embodiments, including the one illustrated in FIG. 1, the drug delivery device 10 may be configured as a wearable drug delivery device, such as an on-body injector or an ambulatory infusion pump, that may be releasably coupled with a patient (e.g., to a patient's tissue 11 such as the patient's skin). In other embodiments, the drug delivery device 10 may be in the form of an autoinjector, a pen injector, or any other type of handheld devices including hybrids thereof. The drug delivery device 10 may be operated to subcutaneously or transdermally deliver a drug to a patient. The drug delivery device 10 may be configured to automatically deliver a fixed or a patient/operator-settable dose of a drug over a fixed and/or a patient/operator-settable period of time. The drug delivery device 10 may be intended for self-administration by the patient, and in some examples, may be used by a caregiver or a formally trained healthcare provider to administer an injection.

The drug delivery device 10 has a housing 12 that is releasably coupled with the patient's tissue 11 and that defines a shell and having an inner volume 12*a*, an activation mechanism 20, a container 30, a needle insertion mechanism (NIM) 100, which incorporates a valve mechanism 150 (e.g., a slide valve mechanism), each of which may be at least partially disposed within the housing 12. It is appreciated that the releasable coupling between the housing 12 and the patient's skin 11 can include any coupling or couplings that allow the drug delivery device 10 to be selectively secured to the patient, including the user holding the device 10 against the injection site, a suction force, an adhesive, or other means of holding the device 10 to the patient such as, for example, a strap, a clamp, and/or a bandage. Further, the drug delivery device may include a controller 14 and an actuator 16 (e.g., a depressible button) that is arranged on an exterior of the housing 12.

The container 30 (which, in some examples, may be referred to as a primary container) has a wall 32 that includes an interior surface 32*a* defining an interior volume 33 that accommodates a plunger 34. The plunger 34 is moveably disposed within the container 30 and has a first end 34*a* that includes an interior surface 35. The interior surface 32*a* of the container 30 and the interior surface 35 of the plunger 34 define a reservoir 36 that contains a drug or medicament 38.

The volume of the drug 38 contained in the reservoir 36 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir may be completely or partially filled with the drug or medicament 38. The drug or medicament 38 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The housing 12 may include a bottom wall 12*b* to contact or to be releasably coupled (e.g., adhered with an adhesive) with the patient's skin 11, and a top wall 12*c* including one or more visual feedback mechanisms 13 such as, for example a window, an opening, and/or an illumination system (not illustrated) for viewing the container 30 and the drug or medicament 38 contained therein. The one or more visual feedback mechanisms 13 may also be used to communicate information to the user about the operational state of the drug delivery device 10 and/or the condition of the drug or medicament 38. An opening 40 may be formed in the bottom wall 12*b*, and optionally a pierceable sterile barrier or septum 42 may extend across the opening 40 to seal the interior 12*a* of the housing 12 prior to use. In some embodiments, the pierceable sterile barrier 42 may be omitted, and instead a removable sealing member (not illustrated) may cover and seal the opening 40 prior to use. The exterior of the needle insertion mechanism (NIM) 100 may be defined by a housing (not illustrated) that is separate from the drug delivery device housing 12.

A fluid flow connection 18 connects the container 30, and more specifically the reservoir 36, to the needle insertion mechanism (NIM) 100. The actuator 16 is configured to initiate operation of the drug delivery device 10 by activating, via mechanical and/or electrical means (shown in dotted lines in FIG. 1), the activation mechanism 20, the needle insertion mechanism (NIM) 100, the controller 14, and/or other mechanisms and/or electronics. In some examples, wireless communication may be employed to cause the drug delivery device 10 to be activated. In embodiments where the actuator 16 is a button that is depressed or otherwise physically moved by a user or patient, the actuator 16 may be configured to exert a motive force and/or transmit a signal needed to activate the needle insertion mechanism (NIM) 100, the fluid flow connection 18, the activation mechanism 20, the controller 14, and/or other mechanisms. In such embodiments, the actuator 16 may be physically connected to, either directly or indirectly via a mechanical linkage, the needle insertion mechanism (NIM) 100, the activation mechanism 20, the fluid flow connection 18, and/or other mechanisms such that manually depressing or otherwise interacting with the actuator 16 supplies the motive force necessary to activate the needle insertion mechanism (NIM) 100, the activation mechanism 20, the fluid flow connection 18, and/or other mechanisms.

The fluid flow connection 18 defines a sterile fluid flow path 19 between the container 30 and the needle insertion mechanism (NIM) 100. The fluid flow connection 18 may be in the form of a flexible tube member. In some examples, a container access mechanism 50 is coupled to the fluid flow connection 18 and is configured to insert a container needle 52 through a septum 54 associated with and/or covering the container 30 to establish fluid communication between the container 30 and the sterile fluid flow path 19 in response to activation of the drug delivery device 10, for example, via the actuator 16. In the illustrated examples, relative movement between the container 30 and the container access mechanism 50 causes the container needle 52 to pierce the septum 54. In some examples, the container needle 52 may be staked to the container 30 such that the container needle 52 cannot move relative to the wall 32 of the container 30; whereas, in other examples, the container needle 52 may be moveable relative to the container 30 and may access the reservoir 36 of the container 30 by piercing through a septum or other sterile barrier covering an opening in the container 30 during operation or set up the drug delivery device 10. In some examples, the needle insertion mechanism (NIM) 100 and the container 30 and/or other components such as the container access mechanism 50 may be integrated into a single unit, and thus the fluid flow connection 18 may not be included in the drug delivery device 10.

For example, in some embodiments, manually depressing or otherwise moving the actuator 16 may cause the fluid flow connection 18 and the container access mechanism 50 to move towards the container 30, or cause the container 30 to move towards the fluid flow connection 18 and the container access mechanism 50, and thereby cause the container needle 52 to penetrate through the seal member or septum 54, thereby creating a fluid flow path between the reservoir 36 and the fluid flow path 19.

Additionally, or alternatively, the actuator 16 may operate as an input device that transmits an electrical, optical, and/or mechanical signal to the controller 14, which in turn may execute programmable instructions to control operation of the needle insertion mechanism (NIM) 100, the activation mechanism 20, the fluid flow connection 18, and/or other mechanisms. In such embodiments, the controller 14 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 16 and which, in response to a control signal received from the controller 14, exerts the motive force needed to activate the needle insertion mechanism (NIM) 100, the activation mechanism 20, the container access mechanism 50, and/or other mechanisms.

The activation mechanism 20 may include any number of components and/or sub-components to drive, urge, and/or exert a force on the plunger 34 to cause the drug or medicament 38 stored therein to be dispensed therefrom and to operate the needle insertion mechanism (NIM) 100. In some examples, the activation mechanism 20 may use a drive fluid 22 in the form of a compressed $CO_2$ gas or other compressed gas and/or a compressed liquid to drive, urge, and/or exert the force on the plunger 34. The drive fluid 22 may initially be stored within a pressure vessel or other container 21, and the activation mechanism 20 may be configured to release the compressed gas and/or liquid from the pressure vessel or other container 21 by opening a valve (not illustrated), which allows the compressed gas and/or liquid to flow into the container 30. In other examples, the activation mechanism 20 may be in the form of a hydro-pneumatic actuation system whereby a hydraulic and/or pneumatic force is exerted on the drive fluid 22 to move the plunger 34 through the container 30 to expel the drug 38 therefrom. In other examples, the activation mechanism 20 may include any number of resilient members (e.g., springs) that exert an urging force on the plunger 34. Examples of suitable activation mechanisms 20 are described in U.S. App. No. 62/543,058, filed on Aug. 9, 2017, the entire contents of which are incorporated by reference herein. Other examples of suitable activation mechanisms 20 are possible.

With reference generally to FIGS. 2-7, the needle insertion mechanism (NIM) 100 operates in multiple stages to insert a generally hollow introducer needle 102 having a first end 102*a* (which, in some examples, may be closed) and an open second end 102*b* (FIG. 7) and a cannula 104 having a first end 104*a* and a second end 104*b* (FIG. 7) into the user. Generally, the needle insertion mechanism (NIM) 100 includes a movable actuation assembly 130 that moves the needle insertion mechanism (NIM) 100 between a storage state and a first operational state, between the first operational state and a second operational state, and between a second operational state and a third operational state.

More specifically, the needle insertion mechanism (NIM) 100 includes a needle insertion mechanism (NIM) body 101 having a track 101*a*, a needle yoke 110, a cannula yoke 120, and an actuation assembly 130 having an escapement assembly 132, a slide valve mechanism 150, and a rotatable link mechanism 160.

The needle yoke 110 defines a body that is operably coupled to the track 101*a* of the needle insertion mechanism (NIM) body 101 while being movable relative thereto. The needle yoke 110 includes a needle coupling portion 112 to couple the needle 102 thereto (thereby causing the needle 102 to move with the needle yoke 110) and an actuation assembly coupling portion 114 to couple a portion of the actuation assembly 130 thereto. More specifically, in the illustrated example, the needle coupling portion 112 is in the form of a hole or an opening that accepts the second end 102*b* of the needle 102, which has a mounting portion 102*c* attached thereto to receive the fluid flow connection 18. The needle 102 may be coupled to the needle yoke 110 via any number of approaches such as, for example, a friction fit coupling, an adhesive, a threaded coupling, and/or a fastener. Other examples are possible. When the fluid flow connection 18 is coupled to the mounting portion 102*c* of the needle 102, the sterile fluid flow path 19 continues through the needle 102 and allows the drug or medicament 38 to exit at the needle 102. The actuation assembly coupling portion 114 is in the form of an elongated slot or groove having a first end 114*a* and a second end 114*b* and will be discussed in further detail below.

The cannula yoke 120 also defines a body that is also operably coupled to the track 101*a* of the needle insertion mechanism (NIM) body 101 while being movable relative thereto. The cannula yoke 120 includes a valve coupling portion 124 to couple the valve body 126 of the slide valve mechanism 150 thereto (thereby causing the valve body 126 to move with the cannula yoke 120).

In some examples, the cannula yoke 120, and more specifically the valve body 126, may include a cannula coupling portion 126*a* to couple the cannula 104 thereto (thereby causing the cannula 104 to move with the cannula yoke 120 and the valve body 126), a septum coupling portion 126*b* to couple a septum 128 thereto, and a valve chamber 127. More specifically, in the illustrated examples, each of the cannula coupling portion 126*a* and the septum coupling portion 126*b* are in the form of a hole or an opening that accepts the second end 104*b* of the cannula 104 and the septum 128, respectively. In certain examples, the valve body 126 may be integrated into the cannula yoke 120 instead of being a separate component. The cannula 104 and the septum 128 may be coupled to the valve body 126 or the cannula yoke 120 via any number of approaches such as, for example, a friction fit coupling, an adhesive, a threaded coupling, via a fastener or fasteners, etc.

The needle 102 may be constructed of material that is rigid or flexible. In examples where the needle 102 is rigid, the needle 102 may be made of a material that is more rigid and/or harder than the cannula 104. For example, the needle 102 may be made of metal and the cannula 104 may be made of plastic or another polymer. The relative flexibility of the cannula 104 may allow it to be disposed subcutaneously within the patient's tissue 11 for a period of a time without causing pain or discomfort to the patient. In examples where the needle 102 is flexible, the needle 102 may be constructed from a super-elastic material such as nitinol, a polymer, or another material that allows the needle 102 to follow a curved path without sustaining damage. In some examples, the needle 102 may function as a trocar for creating a pathway through the patient's tissue to facilitate insertion of the cannula 104.

Figures 5, 6, 7:
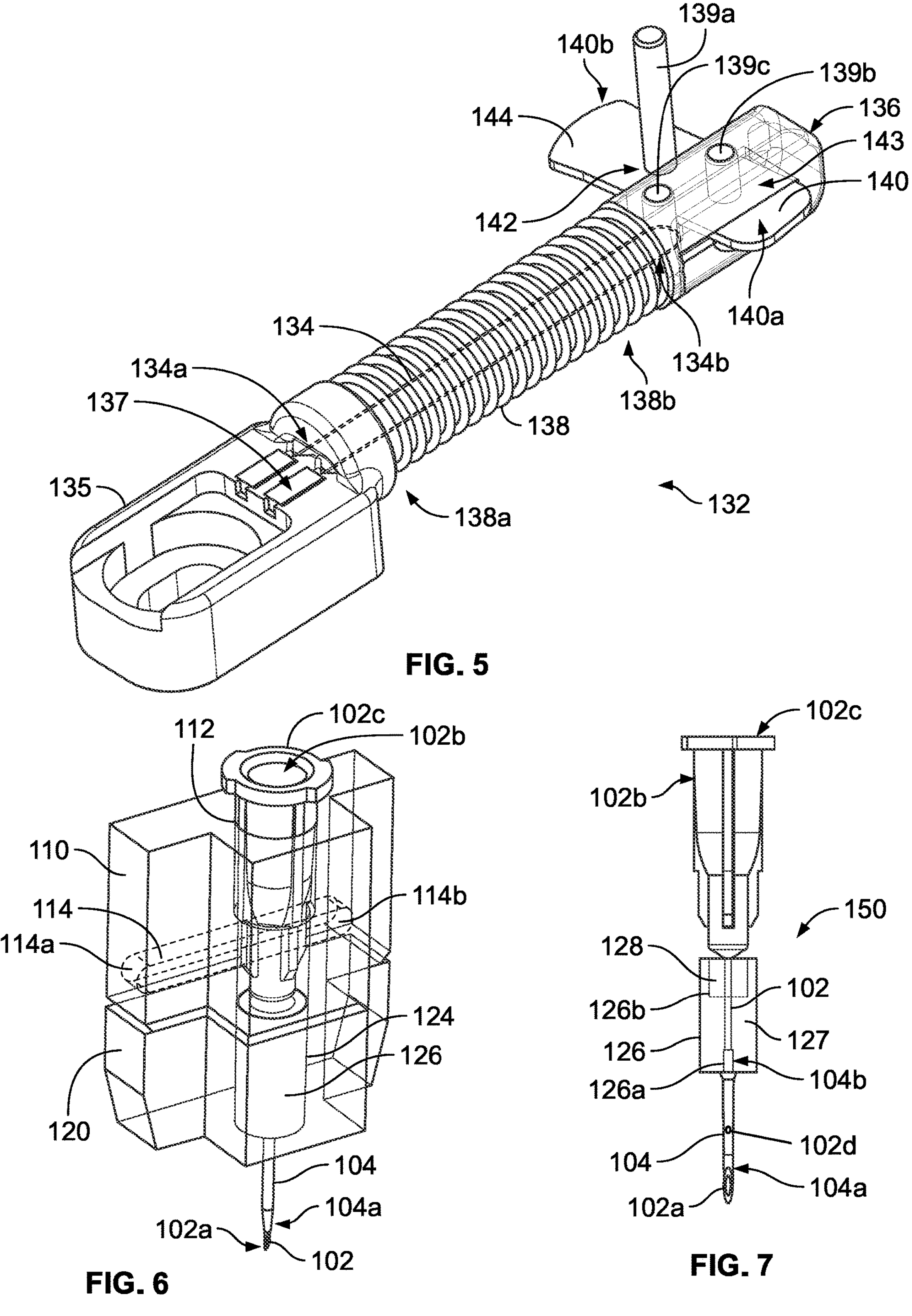
FIG. 5 illustrates an example escapement assembly for the example actuation assembly of FIGS. 2 and 3 in accordance with various embodiments.
FIG. 6 illustrates an example needle yoke and cannula yoke for the example needle insertion mechanism (NIM) of FIGS. 2 and 3 in accordance with various embodiments.
FIG. 7 illustrates an example slide valve mechanism for the example needle insertion mechanism (NIM) of FIGS. 2 and 3 in accordance with various embodiments.

In the illustrated example, the needle 102 is generally hollow to allow the drug or medicament 38 to flow from the second end 102*b* to the first end 102*a* thereof. More specifically, the fluid flow connection 18 is inserted into the mounting portion 102*c* at the second end 102*b* of the needle 102, thereby allowing the drug or medicament 38 to flow through the needle 102. In other examples (not illustrated), the second end 102*b* of the needle 102 may be insertable into the fluid flow connection 18. As can be seen in FIG. 7, the first end 102*a* of the needle 102 can be open or the needle 102 can alternatively include a side port or opening 102*d* to allow the drug or medicament 38 to exit the needle 102. As will be discussed with reference to FIGS. 18-22, immediately or shortly after the cannula 104 has been inserted, the needle 102 may be retracted back towards the housing 12 leaving the cannula 104 within the patient's tissue 11 for subcutaneous delivery of the drug. The cannula 104 is in the form of a generally hollow member that permits fluid flow from the second end 104*b* to the first end 104*a*.

As will be discussed, in some operational states of the needle insertion mechanism (NIM) 100, the side port or opening 102*d* of the needle 102 is positioned within the septum 128, and as such, the slide valve mechanism 150 can selectively seal the opening 102*d* to restrict the drug or medicament 38 from flowing to the cannula 104. In such a configuration, the side opening 102*d* would be open but the first end 102*a* of the needle 102 would be closed. But in other variations, the first end 102*a* of the needle 102 could be open while there would be no side opening 102*d*.

As previously noted, the actuation assembly 130 includes the escapement assembly 132 and the rotatable link mechanism 160. The escapement assembly 132 may be mounted to the body 101 and may include a mounting base 135, a driving member 134, an urging member 138 operably coupled with the driving member 134, an end effector 136, and a pivotable member 140 having one or more pivot pins 139*a* and that may be operably coupled with the urging member 138.

The mounting base 135 may be coupled to the needle insertion mechanism (NIM) body 101 and/or the housing 12 via any number of suitable approaches such as, for example, a friction fit coupling, an adhesive, a threaded coupling, and/or a fastener. In other examples, the mounting base 135 is integrated into the needle insertion mechanism (NIM) body 101 (or the housing 12) instead of being a separate component.

As can be seen in FIG. 5, the driving member 134 is in the form of a linear actuator that includes a first end 134*a* coupled with the mounting base 135 via any number of crimp connectors 137 (or any other suitable fastening mechanism) and a second end 134*b* coupled with the end effector 136 via a coupling pin 139*c* (or any other suitable fastening method). In some examples, the driving member 134 is operably coupled to the actuator 16 and/or the controller 14 via an electrical connection. More specifically, the driving member 134 may be in the form of a muscle wire constructed from nickel-titanium (or a similar) shape-memory alloy that is selectively energized or de-energized during operation of the needle insertion mechanism (NIM) 100. In other examples, the driving member 134 may be in the form of an electromechanical polymer that changes in length in response to an applied electrical current and/or change in temperature. When energized (for example, via a battery), the driving member 134 is adapted to contract, thereby reducing its overall length. The driving member 134 may use any type of coupling such as crimp connectors 137, plugs or other contacts to receive the electrical signal from the actuator 16 and/or the controller 14.

In the illustrated examples, the urging member 138 is in the form of a linear spring (e.g., a compression spring) having a first end 138*a* coupled with (and/or abutting) the mounting base 135 and a second end 138*b* operably coupled with (and/or abutting) the end effector 136. The end effector 136 is operably coupled with a first end 140*a* of the pivotable member 140 via any number of suitable approaches such as a coupling pin 139*b*. In other examples, the urging member 138 may take other forms such as a torsion spring. Other examples are possible.

The pivotable member 140 further includes a second end 140*b*, a first pivot point 142, and a second pivot point 143. The upper surface of the pivotable member 140 defines a platform 144. The first pivot point 142 allows the pivotable member 140 to pivot about the pivot pin 139*a* which is coupled with the needle insertion mechanism (NIM) body 101. The second pivot point 143 further allows the pivotable member 140 to pivot about the coupling pin 139*b*, which is coupled to the end effector 136. In some examples, when the driving member 134 is de-energized, the urging member 138 is configured to urge the pivotable member 140 to a first position. When the driving member 134 is energized, the driving member 134 contracts, thereby compressing the urging member 138 and moving the pivotable member 140 to a second position.

Figure 3:
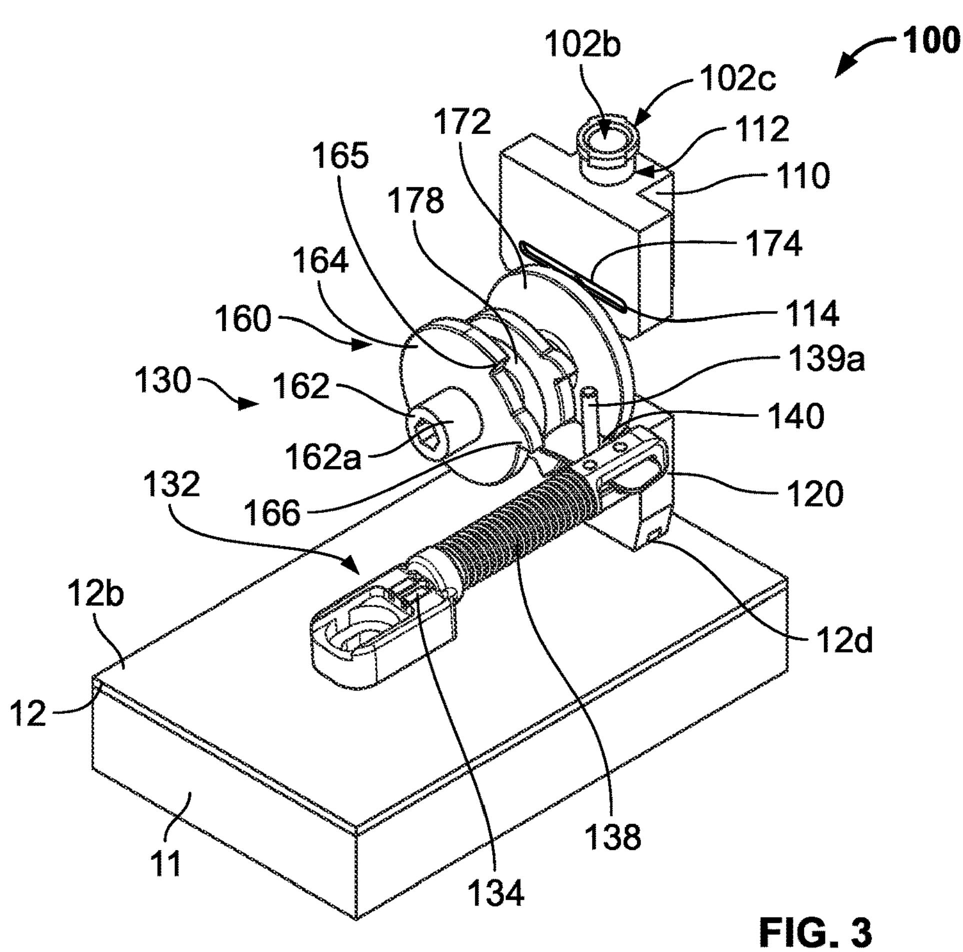
FIG. 3 illustrates the example actuation assembly of FIG. 2 in a flow restricting (valve closed) state in accordance with various embodiments.
Figure 4:
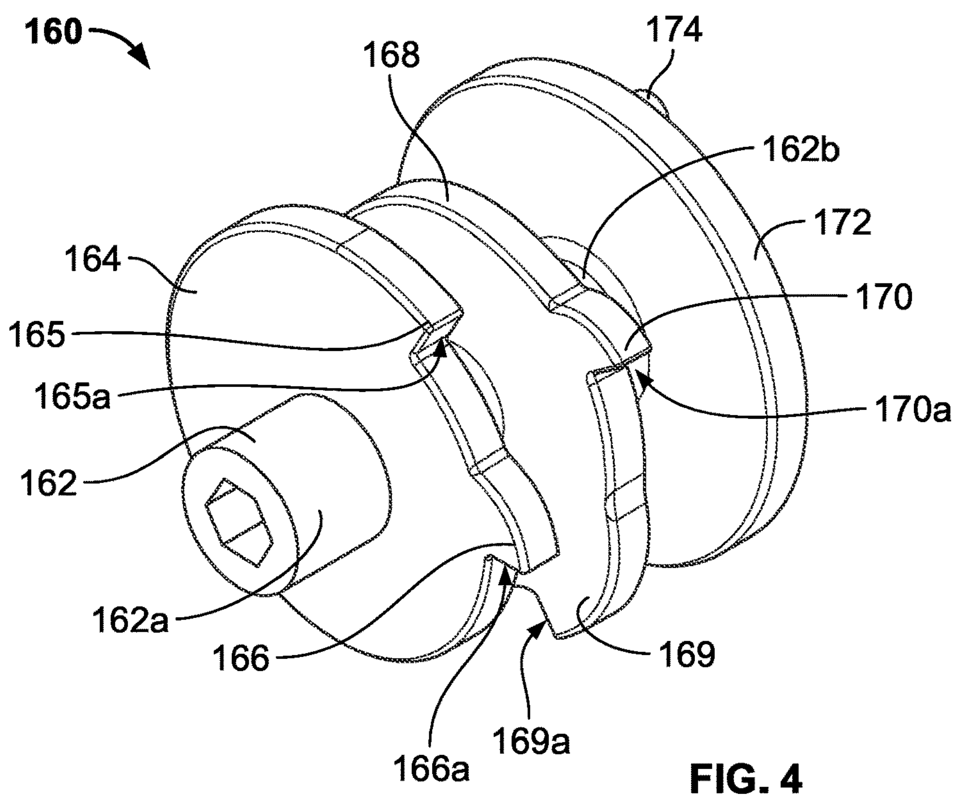
FIG. 4 illustrates an example rotatable link mechanism for the example actuation assembly of FIGS. 2 and 3 in accordance with various embodiments.

As illustrated in FIGS. 3 and 4, the rotatable link mechanism 160 may be in the form of a generally cylindrical scotch yoke spindle body 162 having at least one coupling 162*a* that allows the rotatable link mechanism 160 to couple with (e.g., to rotate within) the needle insertion mechanism (NIM) body 101 (not illustrated in FIG. 3 or 4). In some examples, the scotch yoke spindle body 162 further includes a second coupling 162*b*. The coupling (or couplings) 162*a* may include a cylindrical bearing surface that couple with corresponding bushing members (not illustrated) formed within and/or coupled with the needle insertion mechanism (NIM) body 101. As a result, the rotatable link mechanism 160 may rotate relative to the needle insertion mechanism (NIM) body 101. The rotatable link mechanism 160 further includes a first timing disk 164, a second timing disk 168, and a drive disk 172 having a drive pin 174 extending therefrom. The first timing disk 164 includes a first tab 165 and a second tab 166 extending along an outer edge thereof. Similarly, the second timing disk 168 includes a third tab 169 and a fourth tab 170. Each of the first, second, third, and fourth tabs 165, 166, 169, 170 resemble a ratchet or similar component having respective facing (or radial) surfaces 165*a*, 166*a*, 169*a*, 170*a*. Generally speaking, each of the first timing disk 164, the second timing disk 168, and the drive disk 172 are configured to rotate with the spindle body 162, and as such, the components coupled thereto (or features formed thereon) are also configured to rotate.

Positioned along a length of the spindle body 162 of the rotatable link mechanism 160 is a resilient member 178, which, in the illustrated examples, is in the form of a watch spring. The resilient member 178 serves to exert an urging force on the rotatable link mechanism 160 that causes its rotation. In other examples, the resilient member 178 may take alternate forms such as, for example a torsion spring. Other examples are possible.

The drive pin 174 positioned on the drive disk 172 is configured to be slidably coupled with the needle yoke 110 via the actuation assembly coupling portion 114. More specifically, the drive pin 174 is configured to be inserted into the actuation assembly coupling portion 114.

Generally speaking, a complete injection cycle includes three actions: a first operational state (i.e., insertion of the cannula 104 and the needle 102), a second operational state (i.e., closing of the slide valve mechanism 150), and a third operational state (i.e., opening of the slide valve mechanism 150 to allow for drug administration). For each action, the needle injection mechanism 100 may transition between "active," "passive," and/or "transient" configurations. In some examples, during "passive" states, the rotatable link mechanism 160 is stationary and at a steady state the driving member 134 is not energized, the urging member 138 is extended, and the pivotable member 140 is in the first position. In some examples, during "transient" states, the rotatable link mechanism 160 is moving and not at a steady state, the driving member 134 is energized, the urging member 138 is compressed, and the pivotable member 140 is in the second position. In some examples, during "active" states, the rotatable link mechanism 160 is stationary and at a steady state, the driving member 134 is energized, the urging member 138 is compressed, and the pivotable member 140 is in the second position. Tables summarizing these configurations and states are provided below for ready reference.

In operation, the second end 140*b* of the pivotable member 140 moves between first and second positions to selectively engage the first tab 165, the second tab 166, the third tab 169, and the fourth tab 170 of the first and second timing disks 164, 168. More specifically, the urging member 138 retains the pivotable member 140 in a first position when the signal to the driving member 134 from the actuator 16 and/or the controller 14 is absent. The driving member 134 causes the pivotable member 140 to pivot to the second position when the driving member 134 receives an electrical signal via the actuator 16 and/or the controller 14. The urging member 138 causes the pivotable member 140 to pivot to the first position when the signal to the driving member 134 from the actuator 16 and/or the controller 14 is terminated.

With reference to FIGS. 8-12, the needle insertion mechanism (NIM) 100 begins in a storage state which is "passive" because the driving member 134 is not energized and the rotatable link mechanism 160 is stationary. More specifically, the driving member 134 is in a de-energized, extended state, while the urging member 138 is in an extended state. The urging member 138 exerts a force on the pivotable member 140 and the driving member 134 that is sufficient to move and/or hold the pivotable member 140 in the first position. The resilient member 178 is in a tensioned or loaded configuration that rotatably biases the rotatable link mechanism 160 such that the facing surface 165*a* of the first tab 165 of the first timing disk 164 abuts the platform 144, thereby maintaining the rotatable link mechanism 160 in a stationary position. As illustrated in FIG. 10, the drive pin 174 is disposed at a starting position that is below and to the left of top-dead-center of the drive disk 172 and further is positioned at or near the first end 114*a* of the actuation assembly coupling portion 114. As illustrated in FIGS. 10-12, in this storage state, both the needle yoke 110 and the cannula yoke 120 are in a raised or retracted position, and thus the first ends 102*a*, 104*a* of the needle 102 and the cannula 104, are positioned above the bottom wall 12*b* of the housing 12. Further, in the storage state, the opening 102*d* on the needle 102 is positioned adjacent to, and thus is covered by, a sidewall of the cannula 104.

Turning to FIGS. 13-17, upon engaging the actuator 16, the actuator 16 and/or the controller 14 transmits an electrical signal to the driving member 134 which causes the needle insertion mechanism (NIM) 100 to enter a "transient" configuration moving towards a first operational state. This configuration is "transient" because the driving member 134 is energized and the rotatable link mechanism 160 is in motion.

More specifically, when energized, the driving member 134 contracts, which causes the urging member 138 to compress to in turn cause the pivotable member 140 to pivot to the second position. As the pivotable member 140 moves to the second position, the platform 144 disengages from the facing surface 165*a* of the first tab 165, thereby releasing the rotatable link mechanism 160 from engaging the escapement assembly 132.

As illustrated in FIG. 15, upon disengaging the escapement assembly 132, the rotatable link mechanism 160 is urged by the resilient member 178 to rotate in a direction indicated by arrow "R". As the rotatable link mechanism 160 rotates, the drive pin 174 moves toward bottom-dead-center of the drive disk 172. The motion of causes the drive pin 174 to urge the needle yoke 110 and the cannula yoke 120 downward, thereby moving the needle 102 and the cannula 104 to extended positions where the first ends 102*a*, 104*a* thereof pierce the patient's skin 11 and enter subcutaneous tissue. In this transient configuration the opening 102*d* of the needle 102 remains positioned adjacent to and covered by the sidewall of the cannula 104, and as such, the drug or medicament 38 and/or any other fluids are substantially restricted from entering or exiting the sterile fluid flow path 19. As the drive pin 174 passes through bottom-dead-center, a latching member 12*d* attached to and/or formed by a feature on the bottom wall 12*b* of the housing 12 engages a portion of the cannula yoke 120 to retain and prevent the cannula yoke 120 from moving in an axial direction. Accordingly, the cannula 104 will remain in an extended position in the subcutaneous tissue. In other examples, the latching member 12*d* may instead be attached to (or a feature of) the needle insertion mechanism (NIM) body 101.

With reference to FIGS. 18-22, the needle insertion mechanism (NIM) 100 completes its transition to a first operational state whereby the needle yoke 110, and thus the needle 102, is partially retracted. This first operational state is "active" because the driving member 134 is energized and the rotatable link mechanism 160 is stationary. More specifically, the rotatable link mechanism 160, which may be urged by the resilient member 178, continues to rotate in the direction "R" until reaching a first position illustrated in FIG. 18 where the facing surface 169*a* of the third tab 169 (disposed on the second timing disk 168) abuts and engages the platform 144.

As illustrated in FIG. 20, the rotation of the rotatable link mechanism 160 causes the drive pin 174 to move to a first raised position "ahead" (i.e., below and to the right) of top-dead-center. In this first position, the drive pin 174 is positioned near the second end 114*b* of the actuation assembly coupling portion 114. The motion of the drive pin 174 urges the needle yoke 110, and thus the needle 102 coupled thereto, upward to the first position. With reference to FIGS. 21 and 22, in this first position, the opening 102*d* enters the valve body 126, while the cannula 104 remains in the extended position.

With reference to FIGS. 23-26, upon the actuator 16 and/or the controller 14 terminating the electrical signal to the driving member 134, the needle insertion mechanism (NIM) 100 moves to a second operational state whereby the needle 102 is disposed in a flow restricting (valve closed) position. This second operational state is "passive" because the driving member 134 is not energized and the rotatable link mechanism 160 is stationary.

More specifically, when de-energized, the driving member 134 extends and thus allows the urging member 138 to extend, which then urges the pivotable member 140 to return to the first position, as the pivotable member 140 returns to the first position, the platform 144 disengages from the facing surface 169*a* of the third tab 169, which releases the rotatable link mechanism 160 from the escapement assembly 132. This causes the rotatable link mechanism 160, urged by the resilient member 178, to again rotate in the direction "R" until reaching a second position illustrated in FIG. 23 where the facing surface 166*a* of the second tab 166 engages the platform 144, thus halting rotation of the rotatable link mechanism 160.

Figures 23, 24:
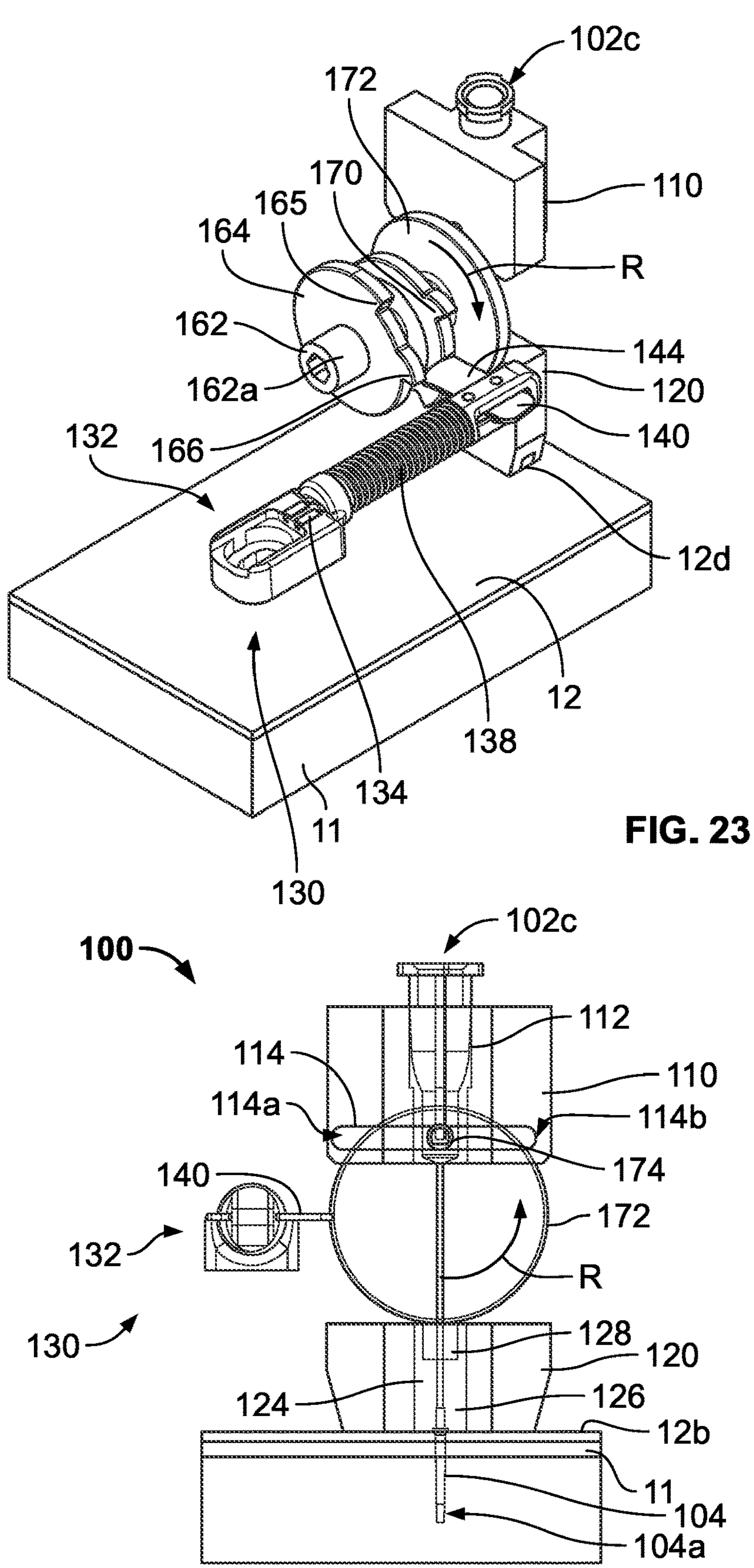
FIG. 23 illustrates a perspective view of the example needle insertion mechanism (NIM) of FIGS. 2-22 in a second operational state in accordance with various embodiments.
FIG. 24 illustrates a side elevation view of a portion of the example needle insertion mechanism (NIM) of FIG. 23 in the second operational state in accordance with various embodiments.
Figures 25, 26:
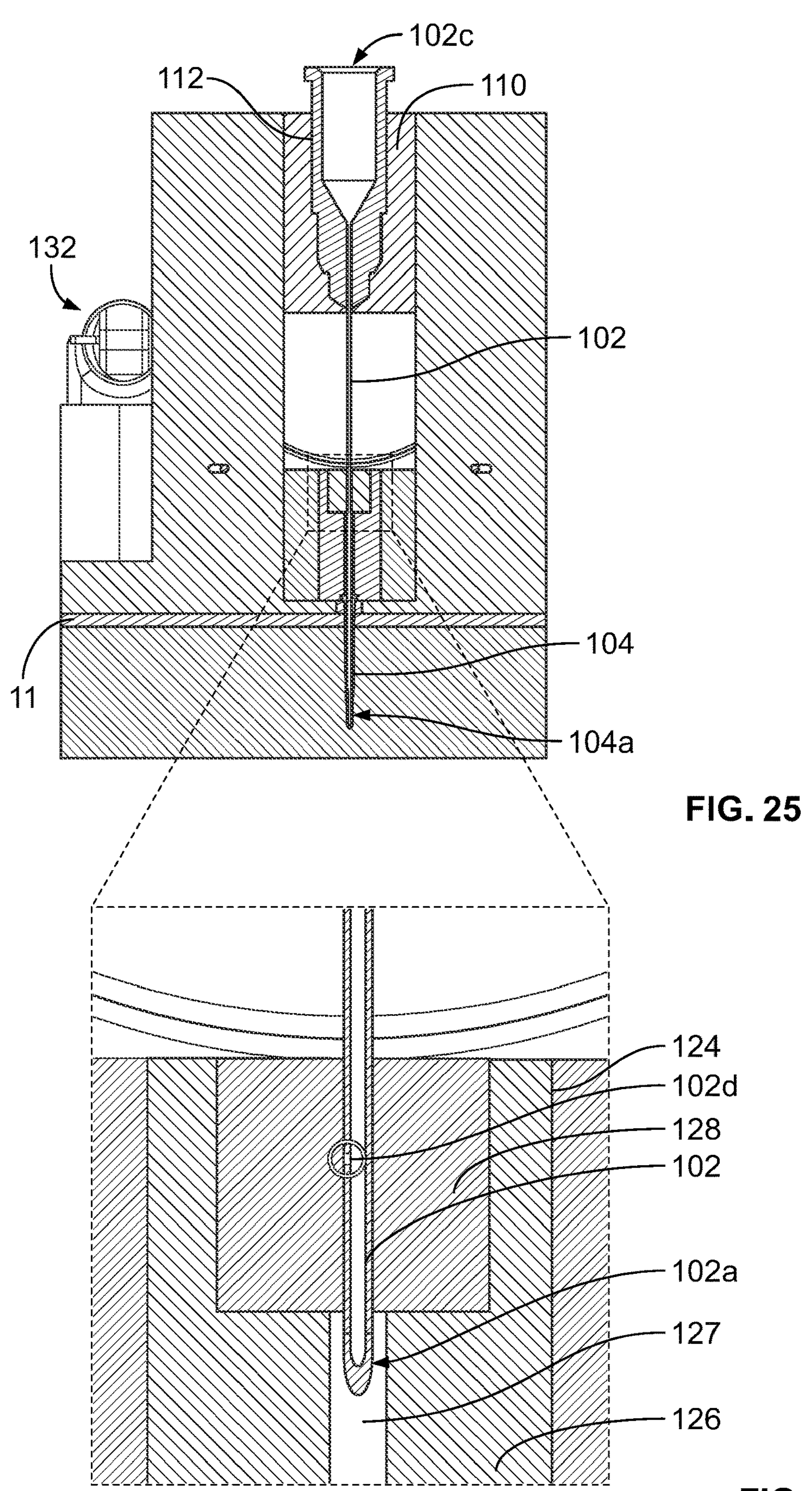
FIG. 25 illustrates a side elevation sectioned view of a portion of the example needle insertion mechanism (NIM) of FIGS. 23 and 24 in the second operational state in accordance with various embodiments.
FIG. 26 illustrates a close-up side elevation sectioned view of the example needle insertion mechanism (NIM) of FIGS. 23-25 in the second operational state in accordance with various embodiments.

As illustrated in FIG. 24, the rotation of the rotatable link mechanism 160 moves the drive pin 174 to a second position at top-dead-center. The motion of the drive pin 174 urges the needle yoke 110, and thus the needle 102, upward to a second position. As illustrated in FIGS. 25 and 26, in this second ("fully raised") position, the opening 102*d* of the needle 102 engages and/or is positioned within the septum 128, which hydraulically disconnects the cannula 104 from the remainder of the sterile fluid flow path 19. In other examples where the needle 102 has an open first end 102*a* (e.g., a bevel-tip needle) the opening 102*d* may be omitted, and the needle insertion mechanism (NIM) 100 may be configured to hydraulically disconnect the cannula 104 from the remainder of the sterile fluid flow path by positioning the first end 102*a* of the needle 102 within the septum 128.

A delay prior to delivery of the drug or medicament 38 may be implemented if desired and/or necessary for the specific drug or medicament 38 being administered. During this delay period, the system remains in the flow restricting (valve closed) state. Because the slide valve mechanism 150 is closed, blood and/or other bodily fluids are restricted from entering the sterile fluid flow path 19, thereby reducing a likelihood of clogs and/or clots in the sterile fluid flow path 19.

With reference to FIGS. 27-30, when administration of the drug or medicament 38 is desired, the actuator 16 and/or the controller 14 again transmits an electrical signal to the driving member 134 which causes needle insertion mechanism (NIM) 100 to move to an intermediate configuration whereby the needle yoke 110, and thus the needle 102, is partially extended. This intermediate configuration is "active" because the driving member 134 is energized and the rotatable link mechanism 160 is stationary.

More specifically, when energized, the driving member 134 contracts, thus compressing the urging member 138 and again rotating the pivotable member 140 to the second position. As the pivotable member 140 moves to the second position, the platform 144 of the pivotable member 140 disengages from the facing surface 166*a* of the second tab 166, which releases the rotatable link mechanism 160 from the escapement assembly 132. This causes the rotatable link mechanism 160, urged by the resilient member 178, to again rotate in the direction "R" until the facing surface 170*a* of the fourth tab 170 engages the platform 144.

Figures 27, 28:
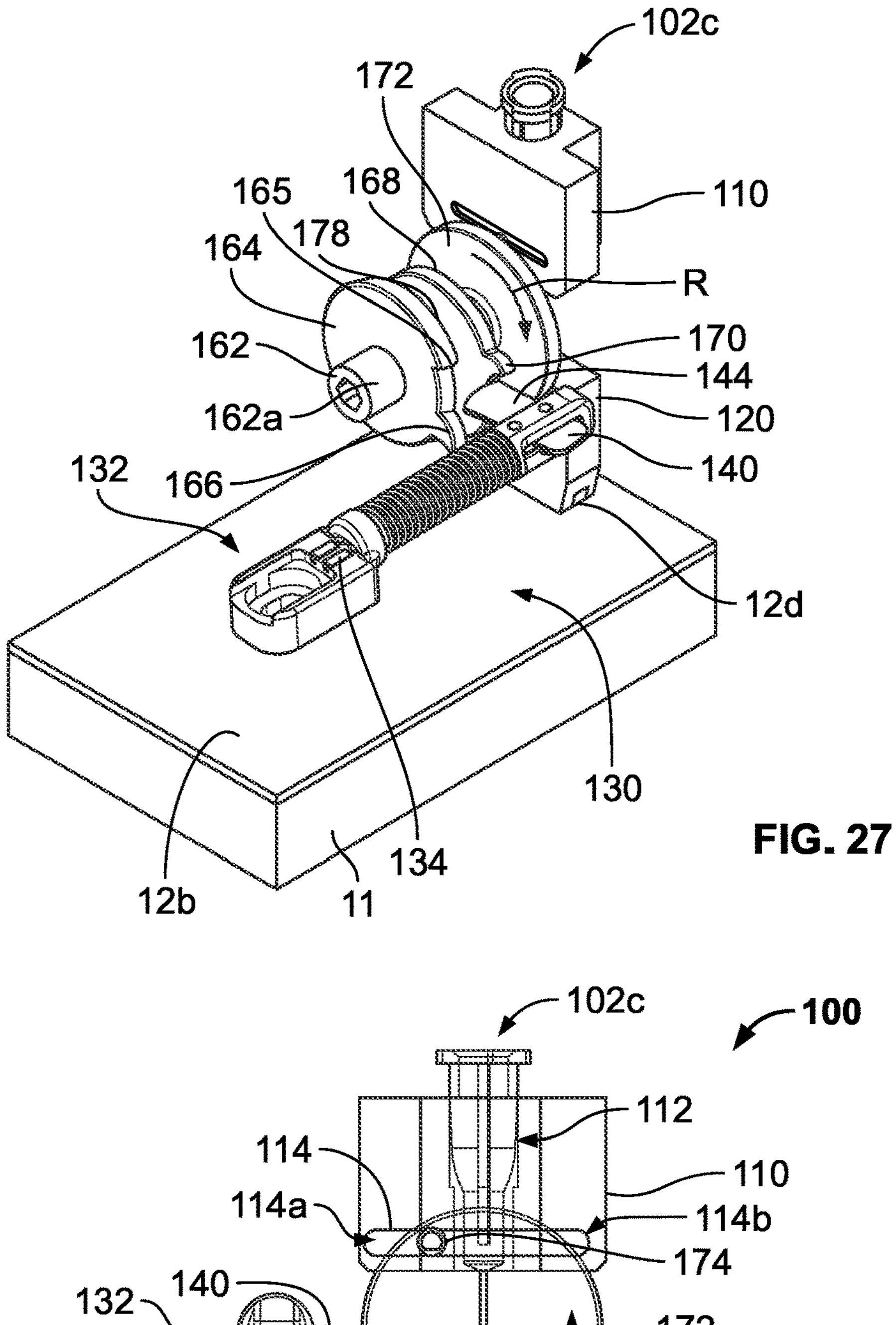
FIG. 27 illustrates a perspective view of the example needle insertion mechanism (NIM) of FIGS. 2-26 during a transition to a third operational state in accordance with various embodiments.
FIG. 28 illustrates a side elevation view of a portion of the example needle insertion mechanism (NIM) of FIG. 27 in the transition to the third operational state in accordance with various embodiments.
Figures 29, 30:
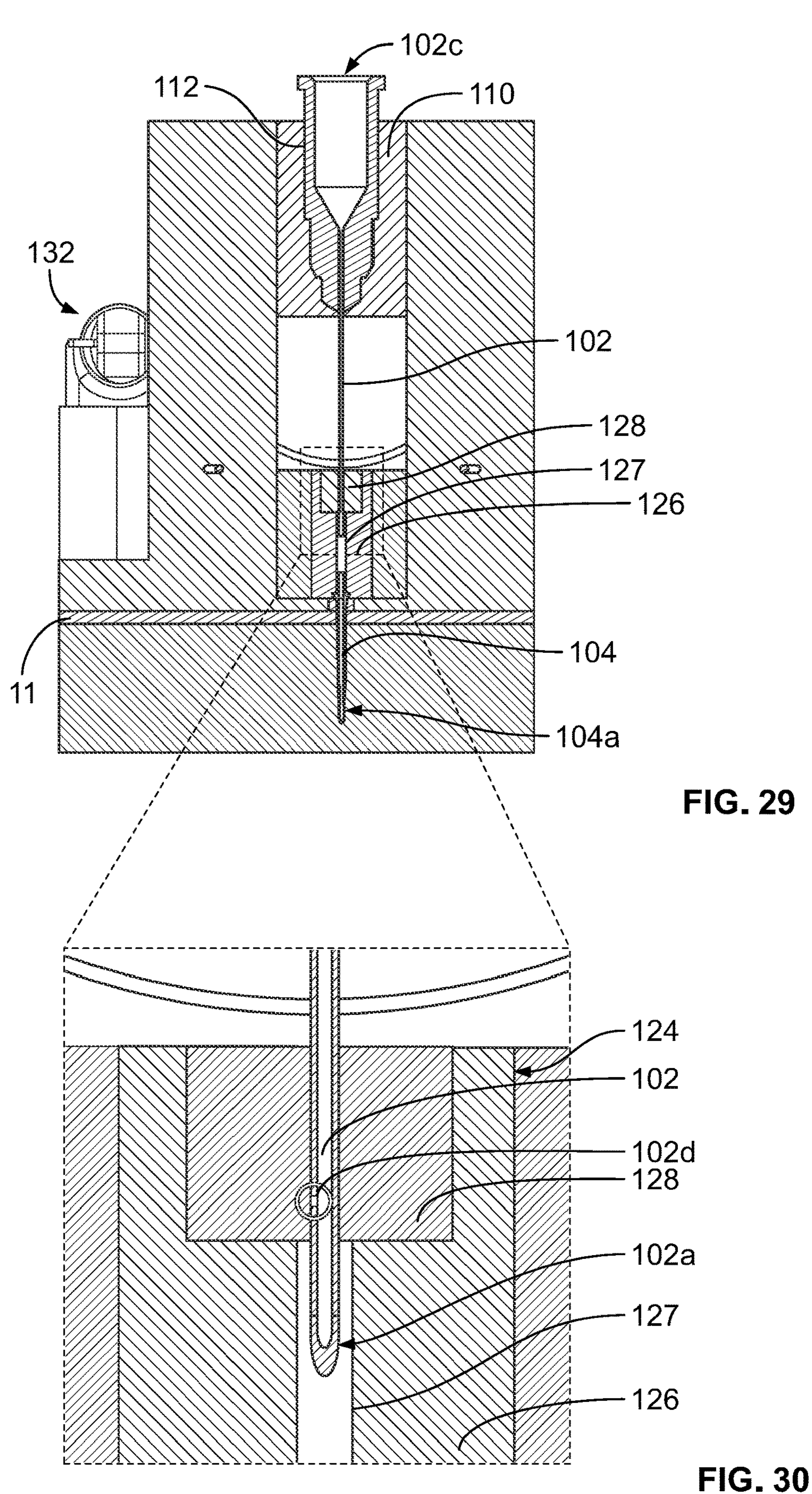
FIG. 29 illustrates a side elevation sectioned view of a portion of the example needle insertion mechanism (NIM) of FIGS. 27 and 28 in the transition to the third operational state in accordance with various embodiments.
FIG. 30 illustrates a close-up side elevation sectioned view of the example needle insertion mechanism (NIM) of FIGS. 27-29 in the transition to the third operational state in accordance with various embodiments.

As illustrated in FIG. 28, the rotation of the rotatable link mechanism 160 moves the drive pin 174 "past" (i.e., below and to the left of) top-dead-center. The motion of the drive pin 174 urges the needle yoke 110, and thus the needle 102, downward to a partially extended position. As illustrated in FIGS. 29 and 30, in this intermediate ("partially extended") position, the opening 102*d* of the needle 102 moves towards the valve chamber 127, but may still be positioned within the septum 128.

With reference to FIGS. 31-35, upon the actuator 16 and/or the controller 14 terminating the electrical signal to the driving member 134, the needle insertion mechanism (NIM) 100 moves to the third operational state whereby the needle 102 is disposed in a flow permitting (valve open) position. This third operational state is "passive" because the driving member 134 is not energized and the rotatable link mechanism 160 is stationary.

More specifically, when the driving member 134 is de-energized, the driving member 134 extends, thereby allowing the urging member 138 to extend, which in turn urges the pivotable member 140 to return to the first position. As the pivotable member 140 returns to the first position, the platform disengages from the facing surface 170*a* of the fourth tab 170, which releases the rotatable link mechanism 160 from the escapement assembly 132. This causes the rotatable link mechanism 160, urged by the resilient member 178, to again rotate in the direction "R" until reaching a third position illustrated in FIG. 32 where the facing surface 165*a* of the first tab 165 again engages the platform 144. In this third operational state, the resilient member 178 may be minimally tensioned (i.e., the resilient member 178 may have a preload force remaining).

Figures 31, 32:
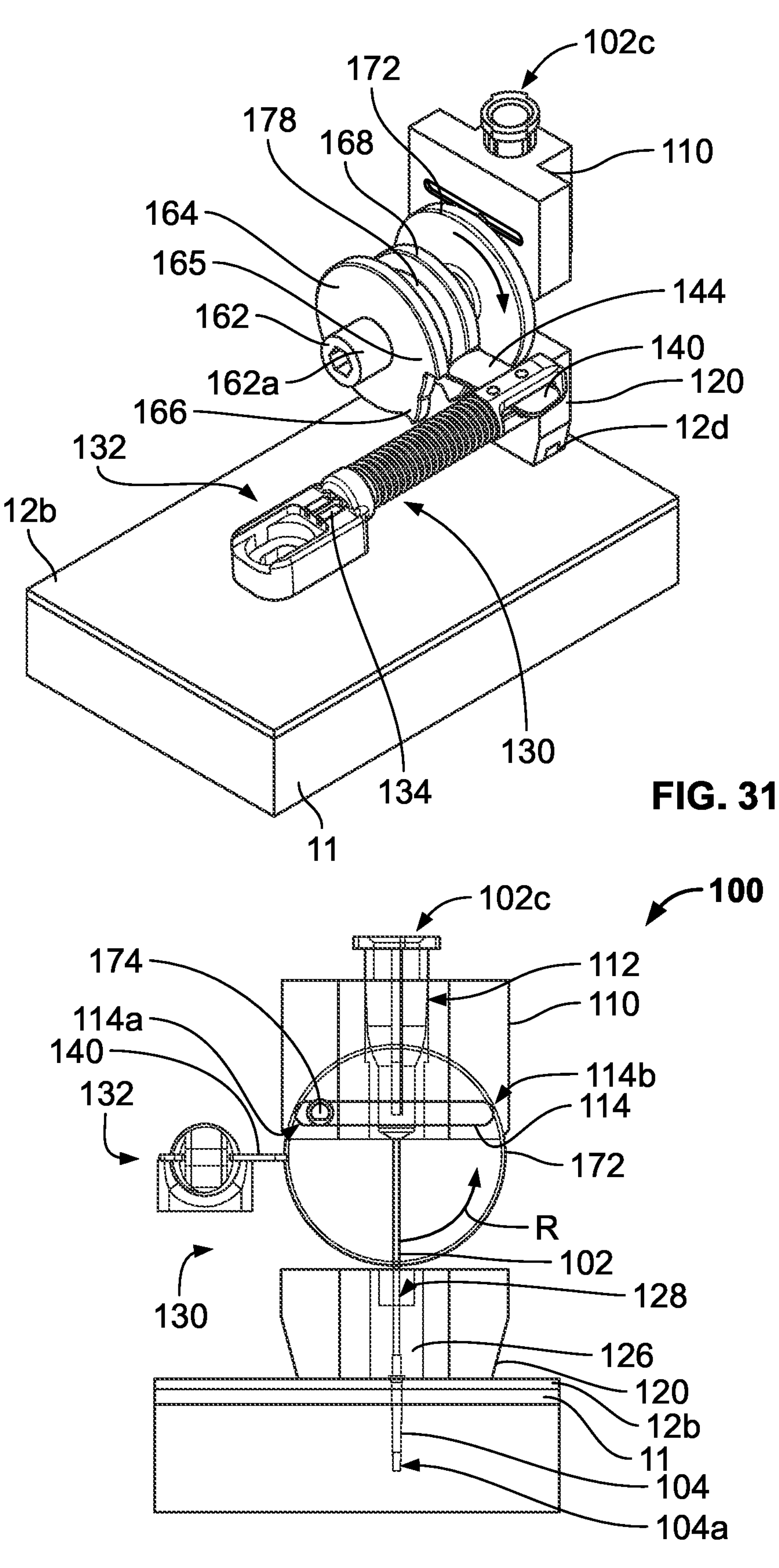
FIG. 31 illustrates a perspective view of the example needle insertion mechanism (NIM) of FIGS. 2-30 in a third operational state in accordance with various embodiments.
FIG. 32 illustrates a side elevation view of a portion of the example needle insertion mechanism (NIM) of FIG. 31 in the third operational state in accordance with various embodiments.
Figures 33, 34, 35:
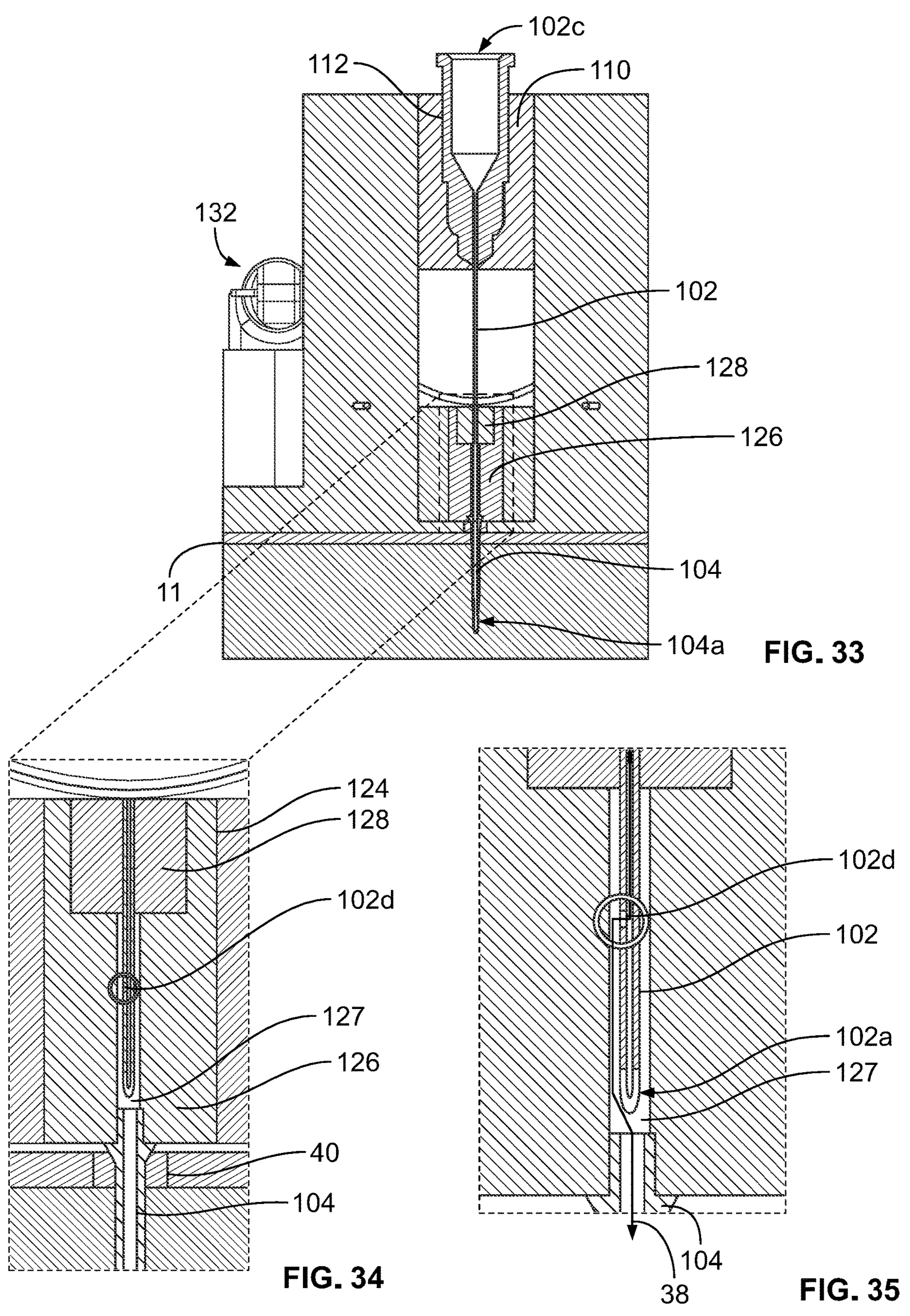
FIG. 33 illustrates a side elevation sectioned view of a portion of the example needle insertion mechanism (NIM) of FIGS. 31 and 32 in the third operational state in accordance with various embodiments.
FIG. 34 illustrates a close-up side elevation sectioned view of the example needle insertion mechanism (NIM) of FIGS. 31-33 in the third operational state in accordance with various embodiments.
FIG. 35 illustrates a close-up side elevation sectioned view of the example needle insertion mechanism (NIM) of FIGS. 2-34 during drug administration in accordance with various embodiments.

As illustrated in FIG. 32, the rotation of the rotatable link mechanism 160 returns the drive pin 174 to the starting position below top-dead-center. The motion of the drive pin 174 urges the needle yoke 110, and thus the needle 102, downward to a flow permitting (valve open) position. As illustrated in FIGS. 33 and 34, in this flow permitting position, the opening 102*d* of the needle 102 is disposed in the valve chamber 127, which opens the slide valve mechanism 150 and hydraulically reconnects the cannula 104 to the remainder of the sterile fluid flow path 19.

In some approaches, if the needle 102 has a closed first end 102*a*, to prevent the first end 102*a* of the needle 102 from blocking flow through the cannula 104, the needle 102 may be configured to not enter the cannula 104 in the flow permitting (valve open) position. However, in examples where the needle 102 has an open first end 102*a* (e.g., a bevel-tip needle), the opening 102*d* may be omitted, and the first end 102*a* of the needle 102 may reenter the cannula 104 without potentially blocking fluid flow.

With reference to FIG. 35, during drug delivery, the needle insertion mechanism (NIM) 100 remains in the third operational state where the valve is open. The drug or medicament 38 exits the needle 102 via the opening 102*d*, flows through the valve chamber 127, enters the second end 104*b* of the cannula 104, and exits the first end 104*a* thereof to the patient.

So configured, the slide valve design allows the fluid path of the drug delivery device to be selectively sealed against the ingress of bodily fluids, thus reducing the likelihood of clogs or clots in the fluid path. The slide valve design may be used in primed and/or non-primed (air filled) fluid paths because both may be susceptible to clot formation. However, the slide valve design may be particularly beneficial for on-body injectors having non-primed (air filled) fluid paths because air is easier to displace than liquids, meaning the bodily fluids have an increased likelihood of flowing in the reverse direction and into the drug delivery device, in both primed and non-primed systems, such backflow of bodily fluids can lead to clot formation, which in turn may reduce the size of the flow path which in turn may require increased forces to urge the drug or medicament through the fluid path to be administered. The needle insertion mechanism (NIM) described herein advantageously supports multiple actions for needle insertion and retraction, and provides an optimized fluid path for controlled and delayed drug delivery. The valve described herein is advantageously positioned as close as possible to the first end 104*a* of the inserted cannula 104 in order to minimize the ingress volume of fluids that may potentially enter the fluid path. The needle insertion mechanism (NIM) 100 described herein separates actuation of the valve from the needle insertion process, thereby minimizing the overall height of the needle insertion mechanism (NIM) 100.

In some approaches, any number of alternative components and/or arrangements may be used. For example, in some arrangements, the cannula may be integrated with or may replace the valve body. The septum of the valve may be integrated as a part of a larger flexible boot member that performs additional sealing functions within the device. Further, an open-tip needle without a side port may be used if the septum engagement is sufficiently large. Additionally, other types of needle insertion mechanism (NIM)s may be used to operate the valve if they support at least three operating actions (i.e., cannula insertion, valve closing, and valve opening. Similarly, other types of mechanisms may be used beyond and/or in place of the muscle wire driven escapement and the Scotch yoke rotatable link mechanism.

In any of the described approaches, a complete injection cycle includes three distinct needle insertion mechanism (NIM) 100 actions: insertion of the cannula 104, closing the valve 126 to restrict fluid flow, and opening the valve 126 to permit fluid flow. For each action, the system transitions through one or more needle insertion mechanism (NIM) 100 states. Each state may be described as either active, passive, or transient. Each of these needle insertion mechanism (NIM) states corresponds to one or more top level states.

TABLE 1

NIM actions and system states.

| Action ID | NIM Action | NIM State ID | State Type | Top-Level Device State(s) |
|---|---|---|---|---|
| 1 | Cannula insertion | 1A | Passive | Pre-activation |
| | | 1B | Transient | Cannula insertion |
| | | 1C | Active | Partial needle retraction |
| 2 | Valve closing | 2A | Passive | Valve closed<br>Delay prior to drug delivery |
| 3 | Valve opening | 3A | Active | Partial needle extension |
| | | 3B | Passive | Valve open<br>Drug delivery |

Figures 8, 9:
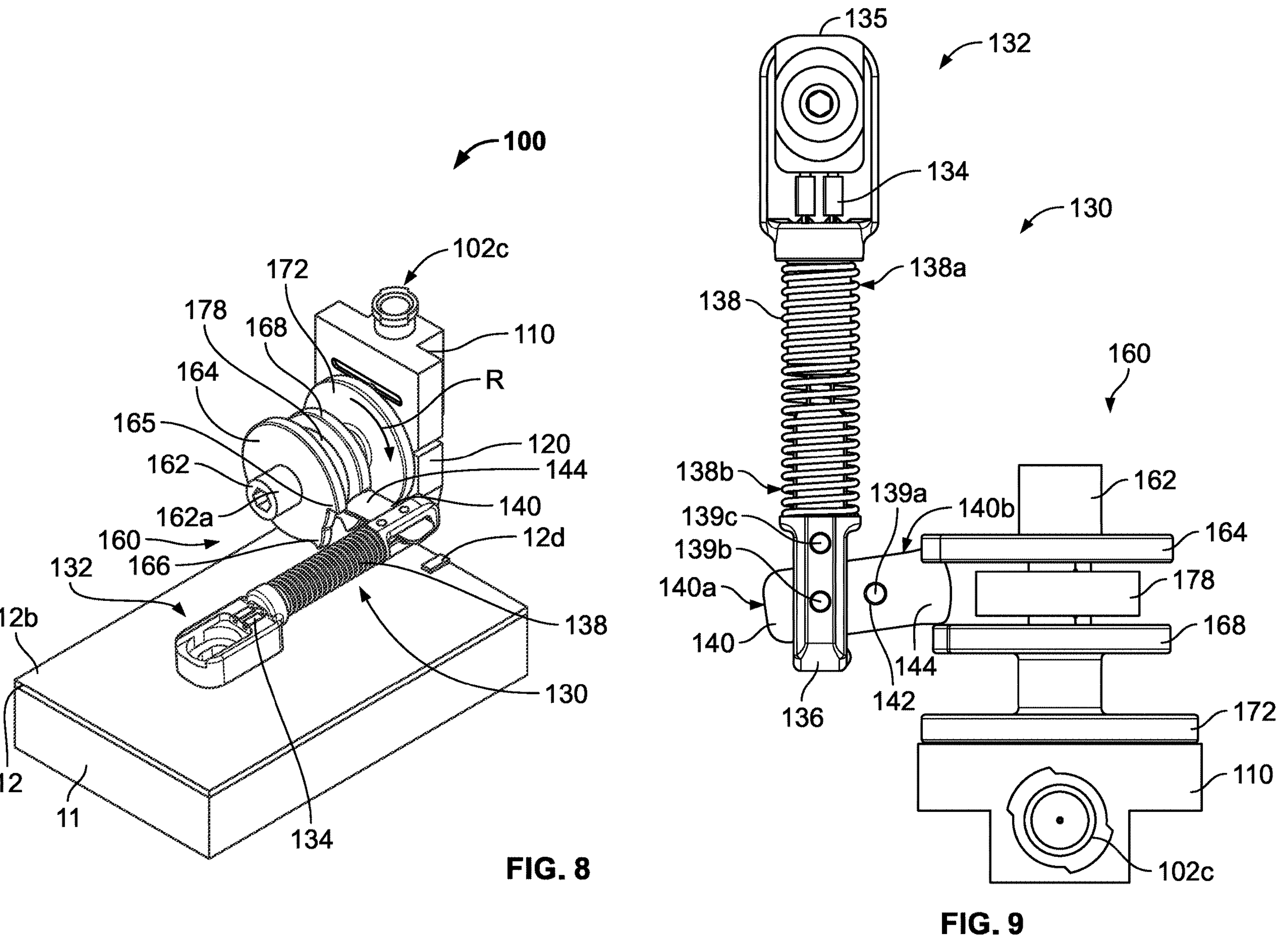
FIG. 8 illustrates a perspective view of the example needle insertion mechanism (NIM) of FIGS. 2-7 in a storage state in accordance with various embodiments.
FIG. 9 illustrates a top plan view of the example needle insertion mechanism (NIM) of FIG. 8 in the storage state in accordance with various embodiments.
Figures 13, 14:
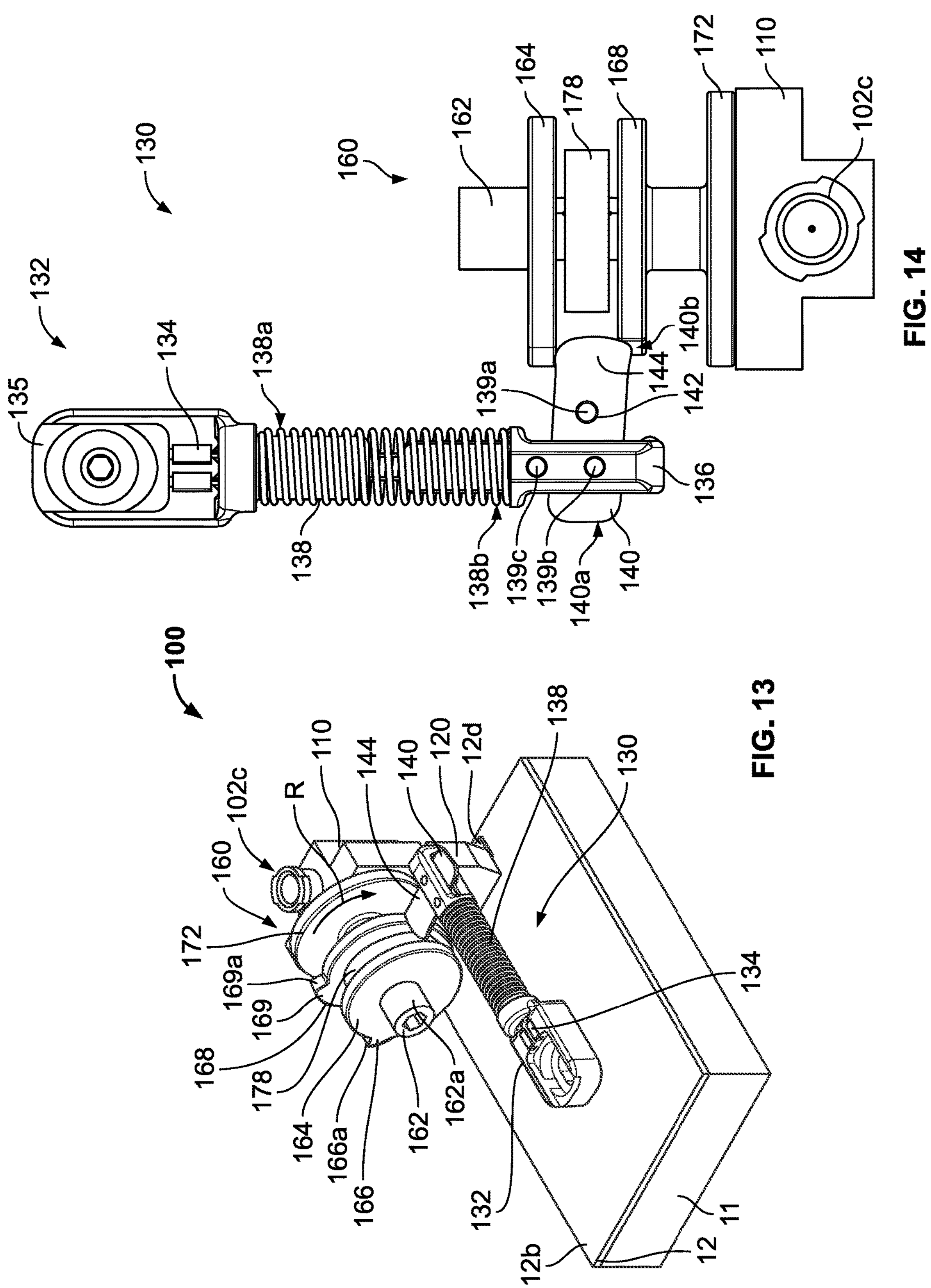
FIG. 13 illustrates a perspective view of the example needle insertion mechanism (NIM) of FIGS. 2-13 in a transitory state in accordance with various embodiments.
FIG. 14 illustrates a top plan view of the example needle insertion mechanism (NIM) of FIG. 13 in the transitory state in accordance with various embodiments.
Figures 18, 19:
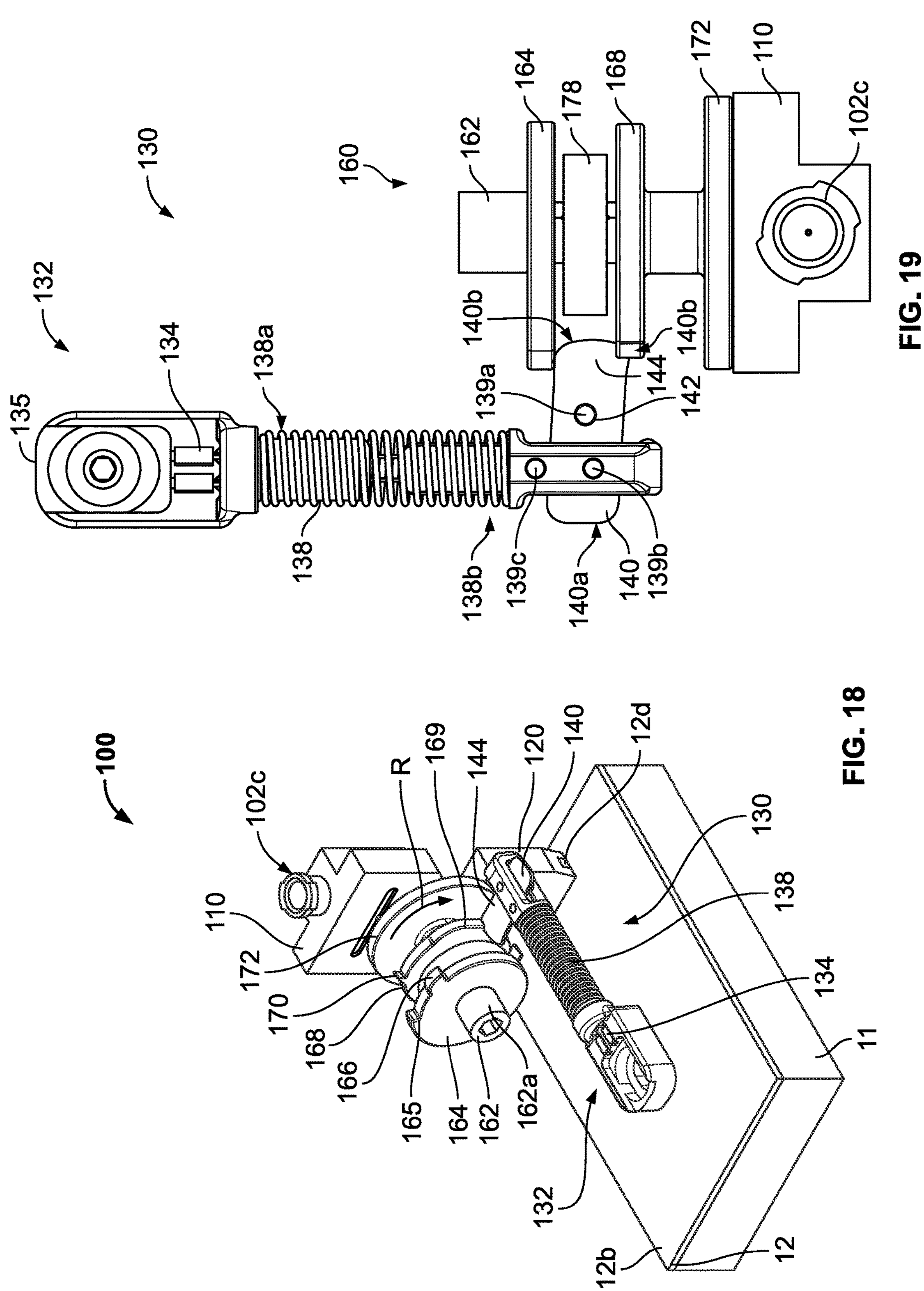
FIG. 18 illustrates a perspective view of the example needle insertion mechanism (NIM) of FIGS. 2-17 in a first operational state in accordance with various embodiments.
FIG. 19 illustrates a top plan view of the example needle insertion mechanism (NIM) of FIG. 18 in the first operational state in accordance with various embodiments.

In the passive state, and as illustrated in FIG. 9, the rotatable link mechanism 160 is stationary at steady state, and the driving member 134 is not energized. In the transient state, and as illustrated in FIG. 14, the rotatable link mechanism 160 is moving at steady state and the driving member 134 is energized. In the active state, and as illustrated in FIG. 19, the rotatable link mechanism 160 is stationary at steady state and the driving member 134 is energized.

The first needle insertion mechanism (NIM) 100 action of cannula insertion includes three needle insertion mechanism (NIM) 100 states: pre-activation, cannula insertion, and partial needle retraction. The pre-activation state (which is illustrated in, for example, FIGS. 8-12) is a passive state because the rotatable link mechanism 160 is stationary and the driving member is not energized. The following Table 2 describes component statuses during the pre-activation state:

TABLE 2

Sub-system status at steady state: pre-activation (State 1A).

| Sub-System | Component/ Assembly | Status |
|---|---|---|
| NIM mechanism | Muscle wire | Not energized |
| | Escapement spring | Extended |
| | Rotary escapement | Engages tab #1 (rear timing plate) |
| | Scotch yoke | Stationary |
| | Drive pin | In starting position |
| | Cannula yoke | Raised |
| | Clock spring | Fully tensioned |
| Fluid path/valve | Needle | In starting position (tip retracted above device floor) |
| | Needle side port | In cannula bore |
| | Cannula | In starting position (tip retracted above device floor) |

The needle 102 and cannula 104 insertion state (which is illustrated in, for example, FIGS. 13-17) is a transient state because the rotatable link mechanism 160 remains in motion. The following Table 3 describes component statuses during the insertion state:

TABLE 3

Sub-system status at bottom dead center: needle/cannula insertion (State 1B)

| Sub-System | Component/ Assembly | Status |
|---|---|---|
| NIM mechanism | Muscle wire | Energized |
| | Escapement spring | Compressed |
| | Rotary escapement | Clear of both timing plates |
| | Scotch yoke | Moving |
| | Drive pin | Moves through bottom dead center without stopping |
| | Cannula yoke | Latches to device floor |
| | Clock spring | Partially tensioned |
| Fluid path/valve | Needle | Enters skin/sub-cutaneous tissue |
| | Needle side port | In cannula bore |
| | Cannula | Enters skin/sub-cutaneous tissue |

The partial needle 102 retraction state (which is illustrated in, for example, FIGS. 18-22) is an active state because the driving member 134 is energized. The following table 4 describes component statuses during the partial needle retraction state:

TABLE 4

Sub-system status at steady state: partial needle retraction (State 1C)

| Sub-System | Component/ Assembly | Status |
|---|---|---|
| NIM mechanism | Muscle wire | Energized |
| | Escapement spring | Compressed |
| | Rotary escapement | Engages tab #2 (front timing plate) |
| | Scotch yoke | Stationary |
| | Drive pin | Below (ahead of) top dead center |
| | Cannula yoke | Latched to device floor |
| | Clock spring | Partially tensioned |
| Fluid path/valve | Needle | Partially retracted |
| | Needle side port | In valve chamber |
| | Cannula | In skin/sub-cutaneous tissue |

During the second needle insertion mechanism (NIM) 100 action of valve 126 closing, the needle insertion mechanism (NIM) is in one state where the valve 126 is closed. This state, which is illustrated in FIGS. 23-26, is a passive state because the rotatable link mechanism 160 is stationary at steady state and the driving member 134 is not energized. The following Table 5 describes component statuses during the valve closing state:

TABLE 5

Sub-system status at steady state: valve closed (State 2A)

| Sub-System | Component/ Assembly | Status |
|---|---|---|
| NIM mechanism (Error! Reference source not found. and Error! Reference source not found.) | Muscle wire | Not energized |
| | Escapement spring | Extended |
| | Rotary escapement | Engages tab #3 (rear timing plate) |
| | Scotch yoke | Stationary |
| | Drive Pin | At top dead center |
| | Cannula yoke | Latched to device floor |
| | Clock spring | Partially tensioned |
| Fluid path/valve (Error! Reference source not found.) | Needle | Fully retracted |
| | Needle side port | Sealed by septum |
| | Cannula | In skin/sub-cutaneous tissue |

The third needle insertion mechanism (NIM) 100 action, valve 126 opening, includes two states: partial needle 102 extension and valve 126 open. The partial needle extension state, which is illustrated in FIGS. 27-30, is an active state because the driving member 134 is energized. The following Table 6 describes component statuses during the partial needle 102 extension state:

TABLE 6

Sub-system status: partial needle extension (State 3A)

| Sub-System | Component/ Assembly | Status |
|---|---|---|
| NIM mechanism | Muscle wire | Energized |
| | Escapement spring | Compressed |
| | Rotary escapement | Engages tab #4 (front timing plate) |
| | Scotch yoke | Stationary |
| | Drive pin | Below (past) top dead center |
| | Cannula yoke | Latched to device floor |
| | Clock spring | Partially tensioned |
| Fluid path/valve | Needle | Partially extended |
| | Needle side port | In bottom part of septum |
| | Cannula | In skin/sub-cutaneous tissue |

The valve 126 open state, which is illustrated in FIGS. 31-35, is a passive state because the rotatable link mechanism 160 is stationary at steady state and the driving member 134 is not energized. The following Table 7 describes component statuses during the valve 126 open state:

TABLE 7

Sub-system status at steady state: valve open (State 3B)

| Sub-System | Component/ Assembly | Status |
|---|---|---|
| NIM mechanism | Muscle wire | Not energized |
| | Escapement spring | Extended |
| | Rotary escapement | Engages tab #1 (rear timing plate) |
| | Scotch yoke | Stationary |
| | Drive pin | In starting position (below top dead center) |
| | Cannula yoke | Latched to device floor |
| | Clock spring | Minimum tension (preload only) |
| Fluid path/valve | Needle | In starting position (tip retracted above device floor) |
| | Needle side port | In valve chamber |
| | Cannula | In skin/sub-cutaneous tissue |

The needle insertion mechanism (NIM) described herein may be provided in any number of alternative designs. For example, FIGS. 36-43 illustrate a second example needle insertion mechanism (NIM) 200 for use with a drug delivery device 10. It is appreciated that the needle insertion mechanism (NIM) 200 illustrated in FIGS. 36-43 may include similar features to the needle insertion mechanism (NIM) 100, and accordingly, elements illustrated in FIGS. 36-43 are designated by similar reference numbers indicated in the embodiment illustrated in FIGS. 1-35 increased by 100. Accordingly, these features will not be described in substantial detail. Further, it is appreciated that any of the elements described with regards to the needle insertion mechanism (NIM) 100 may be incorporated into the needle insertion mechanism (NIM) 200.

In this embodiment, the second end 204*b* of the cannula 204 includes a sealing feature 205. More specifically, as illustrated in FIGS. 37 and 38, the sealing feature 205 of the cannula 204 is in the form of a section having a reduced diameter relative to the remainder of the cannula 204. With reference to FIG. 36, when the needle insertion mechanism (NIM) 200 is in the storage (and passive) state, the drive pin 274 is positioned within the actuation assembly coupling portion 214 and is at top-dead-center relative to the drive disk 272.

Figures 40, 41, 42, 43:
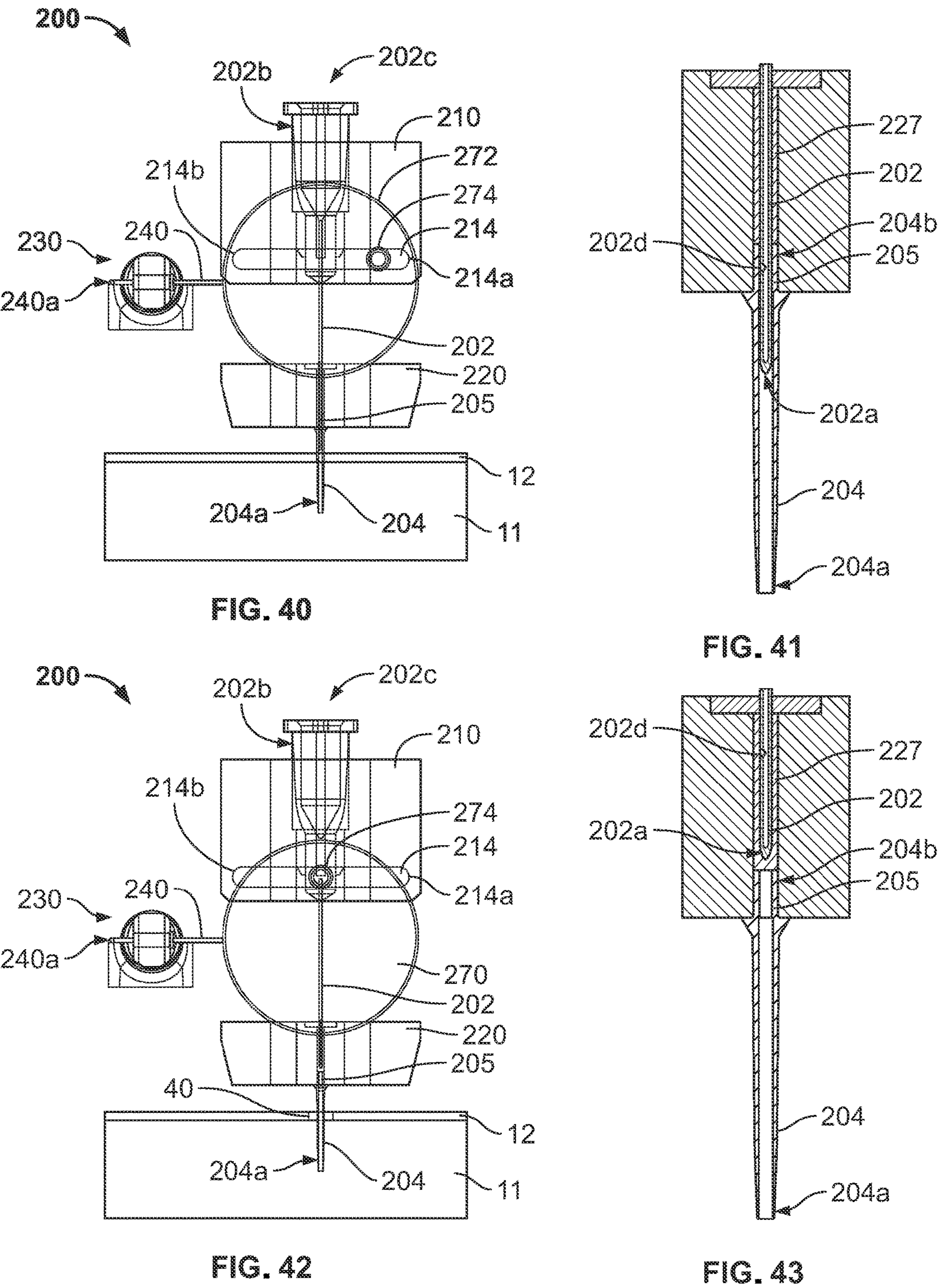
FIG. 40 illustrates a side elevation view of the second example needle insertion mechanism (NIM) of FIGS. 36-39 in a valve closed state in accordance with various embodiments.
FIG. 41 illustrates a close-up elevation sectioned view of view of the second example needle insertion mechanism (NIM) of FIGS. 36-40 in the valve closed state in accordance with various embodiments.
FIG. 42 illustrates a side elevation view of the second example needle insertion mechanism (NIM) of FIGS. 36-41 in a valve open state in accordance with various embodiments.
FIG. 43 illustrates a close-up elevation sectioned view of view of the second example needle insertion mechanism (NIM) of FIGS. 36-42 in the valve open state in accordance with various embodiments.

As illustrated in FIG. 39, during the needle 202/cannula 204 insertion state, the drive pin 274 is in the transient state and moves through bottom-dead-center of the drive disk 272. As illustrated in FIGS. 40 and 41, the needle insertion mechanism (NIM) 200 moves to the flow restricting (valve closed) position, the drive pin 274 is positioned ahead (i.e., to the right of) top-dead-center of the drive disk 272. Movement of the drive pin 274 urges the needle yoke 210, and thus the needle 202, upward to a position where the opening 202*d* of the needle 202 engages and/or is positioned within the sealing feature 205, which hydraulically disconnects the cannula 204 from the remainder of the sterile fluid flow path 19.

With reference to FIGS. 42 and 43, the needle insertion mechanism (NIM) 200 moves to the third operational state whereby the needle 202 is disposed in a flow permitting (valve opening) position. Here, the drive pin 274 moves to a top-dead-center of the drive disk 272, which causes the drive pin 274 to urge the needle yoke 210, and thus the needle 202, upward to a "fully raised" position where the opening 202*d* of the needle 202 is disposed in the valve chamber 227 and is not in contact with the sealing feature 205. As a result, the cannula 204 is hydraulically connected to the remainder of the sterile fluid flow path 19.

By incorporating the sealing feature 205 into the cannula 204, a valve body 226 and a septum 228 may be used that have reduced thicknesses because the septum 228 is not used to seal the side port 202*d* of the needle 202.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIia receptor monoclonal antibody); Actemra® (anti-IL6 Receptor mAb); Avastin® (bevacizumab), HuMax-CD4

(zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-?4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFN? mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF ? monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRASG12C small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:

a housing defining a shell having a bottom wall and an inner volume;

a container at least partially disposed within the housing, the container having an inner volume to contain a medicament;

an activation mechanism at least partially disposed within the housing, the activation mechanism adapted to exert a force to urge the medicament out the container; and a needle insertion mechanism at least partially disposed within the housing and operably coupled with the activation mechanism, the needle insertion mechanism including an actuation assembly adapted to insert a needle and a cannula to deliver the medicament and further including a valve mechanism;

wherein the actuation assembly is movable between a storage state in which each of the needle and the cannula are positioned above the bottom wall of the housing, a first operational state in which the cannula is in an extended position and the needle is in a partially retracted position relative to the extended position, a second operational state in which the cannula remains in the extended position and the needle is disposed in a fully-raised valve closed position, and a third operational state in which the cannula remains in the extended position and the needle is disposed in a lowered, valve opened position.

2. The drug delivery device of claim 1, wherein the actuation assembly is adapted to move the needle and the cannula to the extended position, the partially retracted position, the fully-raised, valve closed position, and the lowered position.

3. The drug delivery device of claim 1, wherein the actuation assembly comprises:

an escapement assembly having a driving member, an urging member operably coupled with the driving member, and a pivotable member operably coupled with the urging member; and a rotatable link mechanism selectively coupled with the pivotable member of the escapement assembly, the rotatable link mechanism being rotatable between a storage position, a first position, a second position, and a third position.

4. The drug delivery device of claim 3, wherein the driving member comprises an electromechanical electrode that contracts upon receiving an electrical signal to compress the urging member, thereby selectively pivoting the pivotable member.

5. The drug delivery device of claim 4, wherein the electromechanical electrode comprises a memory wire.

6. The drug delivery device of claim 3, wherein the rotatable link mechanism comprises:

a first timing disk having a first engagement tab and a second engagement tab; and a second timing disk having a third engagement tab and a fourth engagement tab;

wherein the pivotable member selectively engages the first engagement tab, the second engagement tab, the third engagement tab, and the fourth engagement tab to position the actuation assembly between the storage state, the first operational state, the second operational state, and the third operational state.

7. The drug delivery device of claim 6, wherein the rotatable link mechanism further comprises a drive pin, the drive pin being movable between a storage position when the actuation assembly is in the storage state, a first position when the actuation assembly is in the first operational state, a second position when the actuation assembly is in the second operational state, and a third position when the actuation assembly is in the third operational state.

8. The drug delivery device of claim 7, wherein movement of the drive pin selectively moves the needle and the cannula.

9. The drug delivery device of claim 6, further comprising a second resilient member operably coupled with the rotatable link mechanism to urge the rotatable link mechanism from the storage state to the first position, the second position, and the third position.

10. The drug delivery device of claim 1, wherein the needle insertion mechanism further comprises:

a needle yoke operably coupled with the actuation assembly, the needle yoke including a needle coupling portion to receive a portion of the needle;

a cannula yoke operably coupled with the actuation assembly, the cannula yoke including a cannula coupling portion to receive a portion of the cannula.

11. A needle insertion mechanism for a drug delivery device, the needle insertion mechanism comprising:

an actuation assembly having:

an escapement assembly having a driving member, an urging member operably coupled with the driving member, and a pivotable member operably coupled with the urging member; and a rotatable link mechanism selectively coupled with the pivotable member of the escapement assembly;

wherein the actuation assembly is movable between a storage state whereby the rotatable link mechanism is in a stationary storage position, a first operational state whereby the rotatable link mechanism is in a first stationary position, a second operational state whereby the rotatable link mechanism is in a second stationary position, and a third operational state whereby the rotatable link mechanism is in a third stationary position, wherein the third stationary position is different from the stationary storage position.

12. The needle insertion mechanism of claim 11, wherein the driving member comprises an electromechanical electrode that contracts upon receiving an electrical signal to compress the urging member, thereby selectively pivoting the pivotable member.

13. The needle insertion mechanism of claim 12, wherein the electromechanical electrode comprises a memory wire.

14. The needle insertion mechanism of claim 11, wherein the rotatable link mechanism comprises:

a first timing disk having a first engagement tab and a second engagement tab; and a second timing disk having a third engagement tab and a fourth engagement tab;

wherein the pivotable member selectively engages the first engagement tab, the second engagement tab, the third engagement tab, and the fourth engagement tab to move the actuation assembly between the storage state, the first operational state, the second operational state, and the third operational state.

15. The needle insertion mechanism of claim 14, wherein the rotatable link mechanism further comprises a drive pin, the drive pin movable between a storage position when the actuation assembly is in the storage state, a first position when the actuation assembly is in the first operational state, a second position when the actuation assembly is in the second operational state, and a third position when the actuation assembly is in the third operational state.

16. The needle insertion mechanism of claim 11, further comprising a second resilient member operably coupled with the rotatable link mechanism to urge the rotatable link mechanism from the storage state to the first position, the second position, and the third position.

17. The needle insertion mechanism of claim 11, further comprising:

a needle yoke operably coupled with the actuation assembly, the needle yoke including a needle coupling portion to receive a portion of a needle;

a cannula yoke operably coupled with the actuation assembly, the cannula yoke including a cannula coupling portion to receive a portion of a cannula.

18. A needle insertion mechanism for a drug delivery device, the needle insertion mechanism comprising:

an actuation assembly having:

an escapement assembly having a driving member, an urging member operably coupled with the driving member, and a pivotable member operably coupled with the urging member such that the pivotable member rotates relative to the urging member; and a rotatable link mechanism selectively coupled with the pivotable member of the escapement assembly such that when the pivotable member is coupled with the rotatable link mechanism, a position of the rotatable link mechanism is maintained;

wherein the actuation assembly is movable between a storage state whereby the rotatable link mechanism is in a stationary storage position, a first operational state whereby the rotatable link mechanism is in a first stationary position, a second operational state whereby the rotatable link mechanism is in a second stationary position, and a third operational state whereby the rotatable link mechanism is in a third stationary position.

19. The needle insertion mechanism of claim 18, wherein the pivotable member defines a platform configured to engage the rotatable link mechanism such that a position of the rotatable link mechanism is maintained when the platform engages the rotatable link mechanism.

20. The needle insertion mechanism of claim 19, wherein the rotatable link mechanism is maintained in the stationary storage position by the platform and the actuation assembly moves to the first operational state when the platform disengages from the rotatable link mechanism.

* * * * *